(12) United States Patent
Hansson et al.

(10) Patent No.: US 8,888,487 B2
(45) Date of Patent: Nov. 18, 2014

(54) SET OF FIXTURES, AN IMPLANTATION SYSTEM AND A METHOD OF SELECTING A FIXTURE FROM A SET OF FIXTURES

(75) Inventors: Stig Hansson, Askim (SE); Anders Halldin, Mölndal (SE)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 13/444,959

(22) Filed: Apr. 12, 2012

(65) Prior Publication Data

US 2013/0273499 A1   Oct. 17, 2013

Related U.S. Application Data

(60) Provisional application No. 61/475,327, filed on Apr. 14, 2011.

(30) Foreign Application Priority Data

Apr. 14, 2011   (EP) .................................... 11162481

(51) Int. Cl.
*A61C 8/00*   (2006.01)

(52) U.S. Cl.
CPC ............. *A61C 8/0024* (2013.01); *A61C 8/0018* (2013.01); *A61C 8/0022* (2013.01)
USPC .......................................................... 433/174

(58) Field of Classification Search
CPC .. A61C 8/0018; A61C 8/0022; A61C 8/0024; A61C 8/00
USPC .................. 433/172–176, 165, 215, 141, 166
See application file for complete search history.

(56) References Cited

U.S. PATENT DOCUMENTS

| | | | |
|---|---|---|---|
| 5,823,777 A | | 10/1998 | Misch et al. |
| 6,068,632 A | * | 5/2000 | Carchidi et al. ................ 606/79 |
| 6,146,138 A | * | 11/2000 | Dalmau ........................ 433/141 |
| 6,213,771 B1 | * | 4/2001 | Fischer ........................... 433/75 |
| 6,261,096 B1 | * | 7/2001 | Danger et al. ................. 433/165 |
| 6,296,485 B1 | * | 10/2001 | Danger .......................... 433/165 |
| 7,241,144 B2 | * | 7/2007 | Nilo et al. ..................... 433/174 |

(Continued)

FOREIGN PATENT DOCUMENTS

| | | |
|---|---|---|
| CN | 201775688 U | 3/2011 |
| EP | 0997112 A1 | 5/2000 |

(Continued)

OTHER PUBLICATIONS

Cowin, S. (Bone Mechanics Handbook, second edition, Informa Health Care, 2009, pp. 12-1-12-3).

(Continued)

*Primary Examiner* — Cris L Rodriguez
*Assistant Examiner* — Mirayda A Aponte
(74) *Attorney, Agent, or Firm* — David A. Zdurne; Douglas J. Hura; Leana Levin

(57) ABSTRACT

The present invention relates to a set of fixtures for installation in bone tissue. Each fixture provides a static strain to the bone which is different from the static strain provided by the other fixtures of the set. The difference in static strain may be at least with respect to magnitude and/or axial extension. The invention also relates to an implantation system and a method of selecting a fixture from a set of fixtures.

17 Claims, 13 Drawing Sheets

(56) References Cited

U.S. PATENT DOCUMENTS

| | | | |
|---|---|---|---|
| 8,142,190 B2 * | 3/2012 | Anitua Aldecoa | 433/165 |
| 2002/0094508 A1 * | 7/2002 | Lorenzi | 433/165 |
| 2009/0136898 A1 * | 5/2009 | Kim | 433/165 |
| 2009/0142731 A1 * | 6/2009 | Kim | 433/165 |
| 2009/0305189 A1 * | 12/2009 | Scortecci et al. | 433/165 |
| 2011/0070558 A1 | 3/2011 | Park et al. | |

FOREIGN PATENT DOCUMENTS

| | | |
|---|---|---|
| EP | 2292176 A1 | 3/2011 |
| WO | 0003657 A1 | 1/2000 |
| WO | 03015654 A1 | 2/2003 |
| WO | 2005079697 A1 | 9/2005 |
| WO | 2009054005 A2 | 4/2009 |
| WO | 2009054650 A1 | 4/2009 |
| WO | 2009072764 A1 | 6/2009 |

OTHER PUBLICATIONS

European Search Report, Application No. 11162481.3, Published Mar. 2, 2012.

McCalden R.W. et al(Age-related changes in the tensile properties of cortical bone. The Journal of Bone and Joint Surgery, vol. 75-A. No. 8, Aug. 1993).

Gibson, J. Biomechanics, vol. 18, No. 5, pp. 317-328, 1985.

Kold S. et al, Compacted cancellous bone has a spring-back effect. Acta Orthopaedica Scandinavica, 2003; 74(5): 591-595.

International Search Report,Application No. PCT/EP2012?056725,Apr. 4, 2011.

European Search Report, Application No. 11162481.3, Publication Sep. 27, 2011.

* cited by examiner

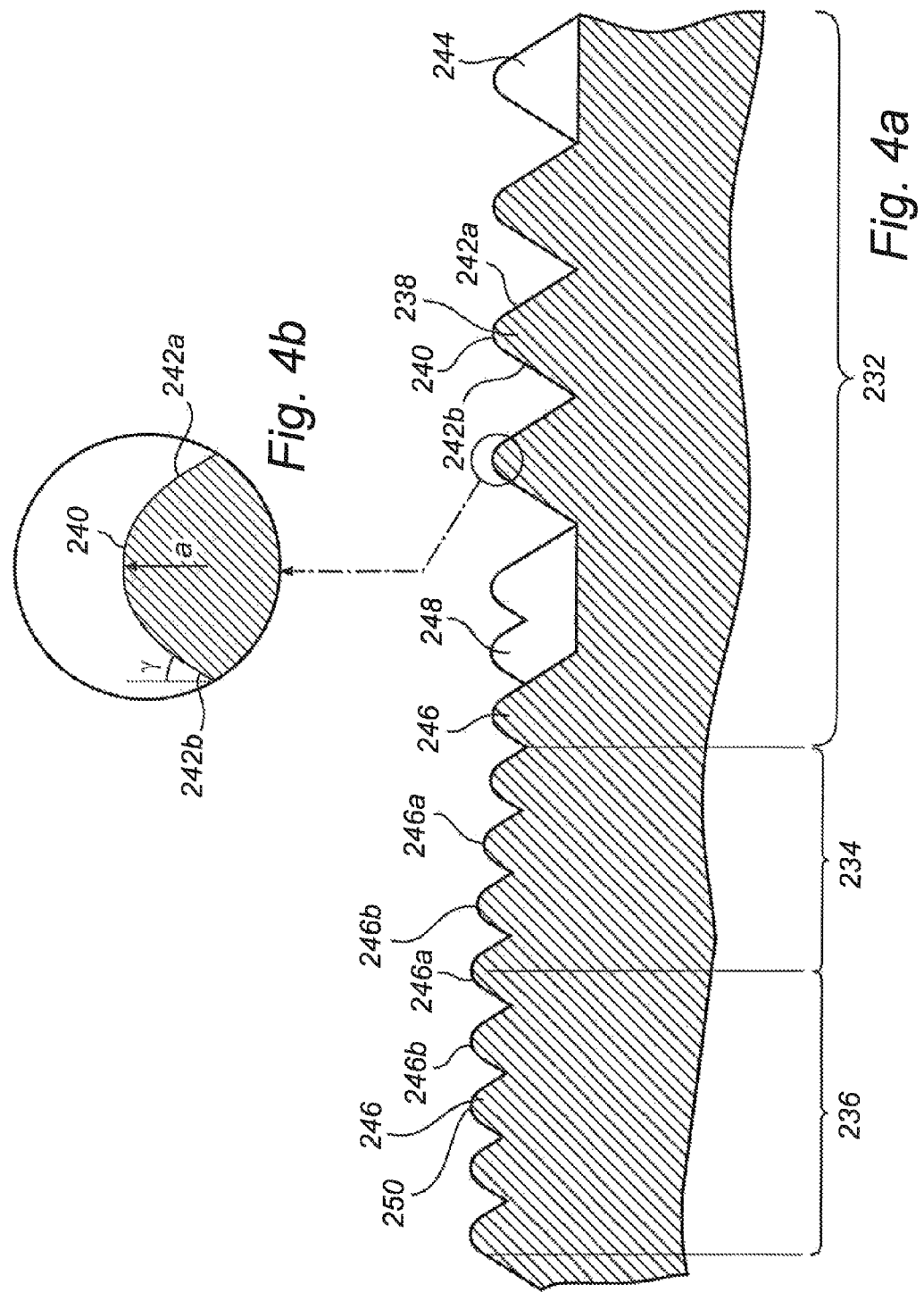

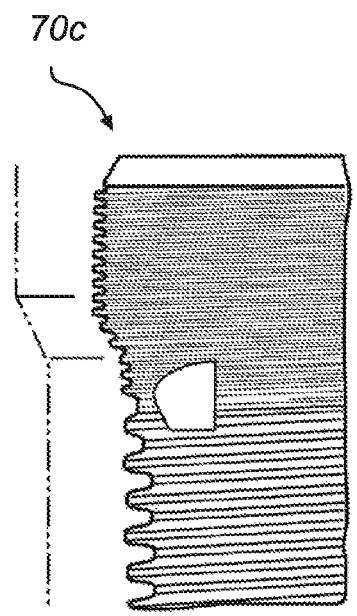
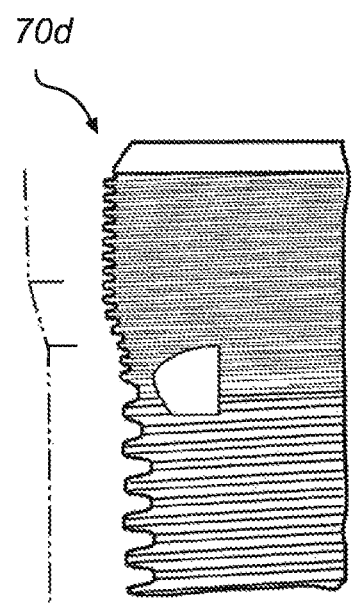
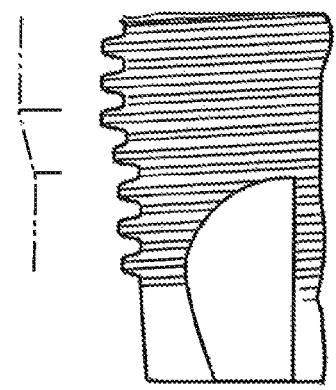
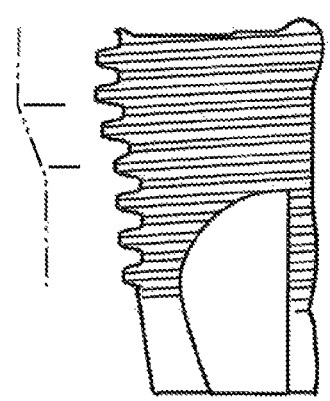
Fig. 7c          Fig. 7d

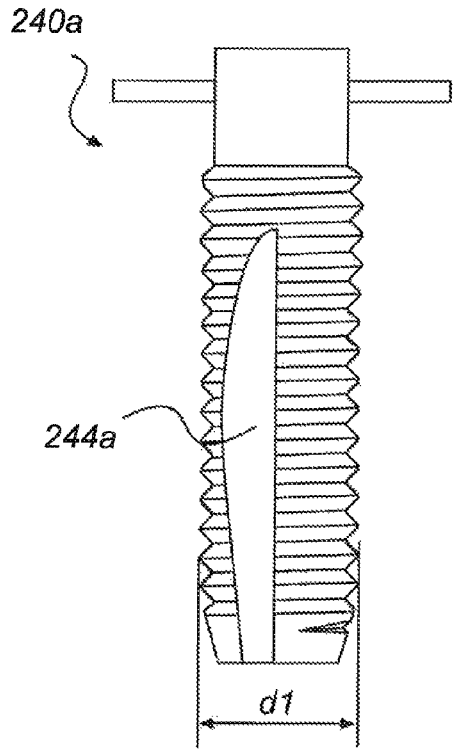
Fig. 9a
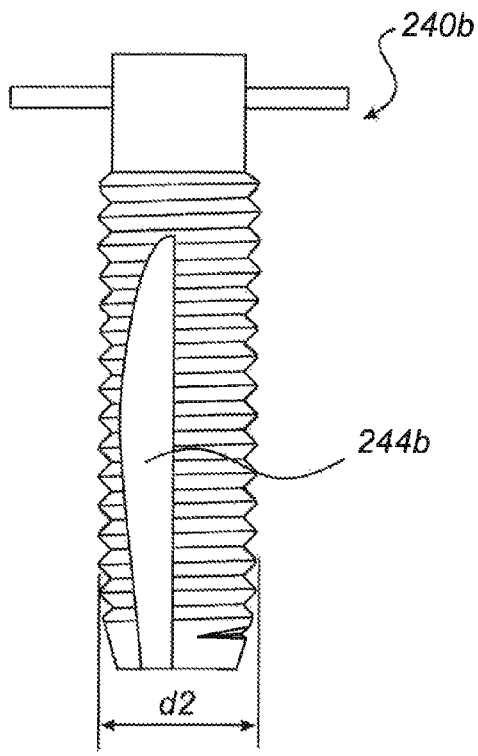
Fig. 9b
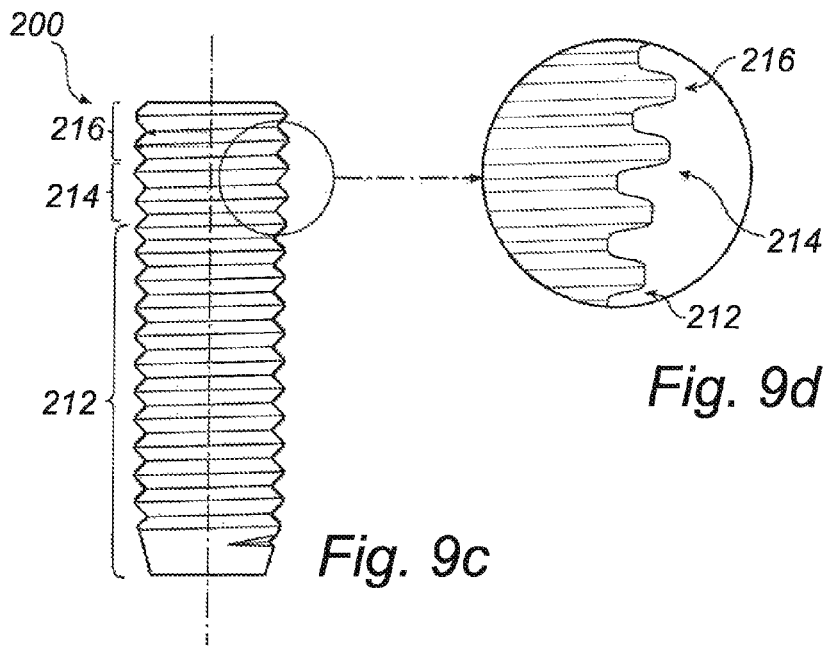
Fig. 9c
Fig. 9d

SET OF FIXTURES, AN IMPLANTATION SYSTEM AND A METHOD OF SELECTING A FIXTURE FROM A SET OF FIXTURES

TECHNICAL FIELD

The present invention relates to a set of fixtures for installation in bone tissue. The set comprises at least a first fixture and a second fixture for insertion into a bore hole arranged in bone tissue. The invention also relates to an implantation system and a method of selecting a fixture from a set of fixtures.

BACKGROUND OF THE INVENTION

A frequent way today to restore a damaged limb, such as lost tooth, is to install a fixture in the adjacent bone tissue and replace the damaged parts. In this respect, for a successful result, the fixture should become fully stable and correctly joined to the bone. The term osseointegration is used for this joining effect, the basic meaning of this term being the bone tissue growth into the fixture surface. The two major contributors to this joint are a mechanical joint and an organic joint. The former being generally influenced by the macro geometry of the bore into which the fixture is installed, and by the macro geometry of the fixture, and is a direct effect of how well these two work together. The latter one being a continuously evolving and developing effect, particularly the time immediately after installation, and being generally influenced by how well the micro surface structure of the fixture interacts with the bone tissue.

Due to ingrowth there will be an interlocking effect between the bone and the fixture. Also, the mechanical joint is developed over time since the bone tissue, under ideal conditions, may grow into surface cavities of the fixture, and grow into voids left between the fixture and the bore after installation.

During installation of a fixture into the bone tissue, the bone is subjected to both stress and strain. The relationship between stress and strain is substantially linear up to a yield point (yield strain). Up to the yield point the bone is deformed elastically. However, beyond the yield point the bone will deform plastically. In order to provide for good healing conditions and stability of the fixture in the bone, care is taken to maintain the elasticity of the bone tissue and to avoid exceeding the yield point.

There is a continuous endeavor in the industry to further increase the stability of fixtures implanted in bone tissue and to improve the basic conditions during the healing phase after fixture installation. One example is the provision of the fixture surface with different types of structures, such as micro-roughened or blasted structures for increasing the contact surface between the fixture and the bone.

Nevertheless, there is till room for further development of fixtures as regards their stability in bone tissue.

SUMMARY OF THE INVENTION

An object of the present invention is to provide a set of fixtures, in particular dental fixtures, which have a high stability/strength during the healing phase of the fixture. This and other objects, which will become apparent in the following, are accomplished by means of a set of fixture defined in the accompanying claims.

The present invention is based on the insight that applying a static strain to the bone tissue during and after implantation may be beneficial to the strength/stability of the fixture during the healing phase of the bone. Actually, the inventors have realized that even strains exceeding the yield point of the bone may be beneficial. In particular, the inventors have found that tensile strains in the circumferential direction which exceed the ultimate strain of the bone, i.e. when the bone cracks, may also be beneficial to trigger the biological response during the healing phase after fixture installation. Although cracks may be formed near the fixture, there will be present stabilizing surrounding bone tissue.

The inventors have further realized that the yield point and ultimate strain of the bone tissue varies from patient to patient, and that selection of fixture should suitably be customized or patient-specific. In other words, by identifying strain-affecting characteristics of a patient or a patient's bone tissue, a fixture providing a suitable strain may be selected from a set of fixtures.

According to a first aspect of the invention, a set of fixtures for installation in bone tissue is provided. The set comprises:

a first fixture for insertion into a bore hole arranged in bone tissue for providing static strain to the bone tissue, and a second fixture for insertion into a bore hole arranged in bone tissue for providing static strain to the bone tissue, wherein the static strain provided by the first fixture if installed into a bore hole is, at least with respect to magnitude and/or axial extension, different from the static strain provided by the second fixture if it would be installed into said bore hole instead of the first fixture.

Thus, depending on e.g. the quality of the patient's bone the most appropriate fixture in the set can be selected for implantation. The selection may, for instance, be based on the person's age, bone density, mineral content of the bone tissue, bone tissue disease or bone thickness.

Of course, it should be understood that the set may include more than two fixtures, e.g. three, four, five, six or even more fixtures, each providing a different static strain. Furthermore, the difference in strain may either be difference in magnitudes, e.g. expressed as a percentage(s), or be difference in axial extensions. This may be advantageous if it is desired to control the strain at a certain part of the bone, e.g. the cortical bone, and depending on the available bone thickness an appropriate fixture can be selected. For instance, the first fixture may provide a static strain which extends 1 mm along the length of the fixture, while the second fixture provide the same magnitude of static strain but along another length, e.g. 2 mm along the length of the fixture. It is also conceivable that the fixture strains differ both with regard to magnitude and axial extension.

The insertion of a fixture with a certain torque means that static strains will be induced in the surrounding bone. The magnitude of these static strains do not only depend on the insertion torque but also depend on the fixture design, the shape of the bone preparation, the bone anatomy, the bone quality and possibly also on the fixture surface topography. Rather than to elaborate on these different parameters, some of which are difficult to estimate, the inventors have ingeniously realized that it is possible to achieve an adequately controlled static strain by fixture design.

In a circular geometry, the tensile strain in the circumferential direction is given by the increase in circumference divided by the initial circumference. For instance, with an initial diameter D the circumference is $\pi \cdot D$. If the diameter is increased by $\Delta D$, then the new circumference becomes $\pi \cdot (D+\Delta D)$. Thus, the increase in circumference is $\pi(D+\Delta D) - \pi \cdot D = \pi \cdot \Delta D$. Dividing the increase in circumference with the initial circumference of $\pi \cdot D$ results in a strain $\Delta D/D$.

By providing a female thread with a first radius r in the bone tissue surrounding the bore hole (the radius being the distance from the bore hole axis to the bone thread) and by providing the fixture with a threaded portion having threads at a second radius R which is larger than the first radius r, a pressure will be applied to the bone when said threaded portion is rotated into the bone via said bone threads. The enlarged radius R will thus lead to a condensation of the bone tissue. In analogy with the above explained strain ΔD/D, the maximum strain will thus be $$\frac{R-r}{r}.$$

This means that by controlling the difference in radius between said threaded fixture portion and the bone thread with which the threads of said portion will mate, a controlled static strain may be achieved.

For instance, by having a threaded leading portion of the fixture with a first radius r corresponding to the radius of the bone threads, i.e. the distance from bore hole axis to the bone threads, and a threaded trailing portion having a second radius R which is larger than said first radius said controlled strain may be achieved.

The bone threads may be achieved either by pre-tapping with a separate tapper or by tapping means, such as cutting edges, on a self-tapping fixture.

According to at least one example embodiment, each one of the fixtures in said set comprises a leading portion, and a trailing portion being wider than the leading portion with respect to major and/or minor diameter for providing the static strain to the bone tissue, wherein at least a subportion of the trailing portion of the first fixture is dimensionally different from a corresponding subportion of the trailing portion of the second fixture. The minor diameter is generally determined by the thread bottoms or core of the fixture, while the major diameter is determined by the thread tops (or more specifically a geometrical circumferential surface which is tangential to the thread tops). Rather than just having a subportion of the trailing portion to be different in the two fixtures, the entire trailing portions may be different. For instance, the trailing portion of the first fixture may have one width, and the entire trailing portion of the second fixture may have a different width.

According to at least one example embodiment, each one of said fixtures comprises an external thread which extends uninterrupted from the leading portion to the trailing portion. Thus, the external thread provides a continuous transition from the leading portion to the trailing portion. Although, for instance, part of the leading portion may have one or more cutting edges which interrupt the external thread, at the area of transition from the leading portion to the trailing portion the thread extends uninterrupted. The uninterrupted external thread may thus be provided on a transition portion arranged between the leading portion and the trailing portion.

According to at least one example embodiment said leading and trailing portions of said fixtures comprise a respective outer surface being threaded for engagement with the bone tissue, wherein thread tops and thread bottoms are provided alternatingly along the axial direction of the fixture, wherein in the trailing portion of the first fixture, the radial distance from the fixture axis to a thread top is $R_{t1}$ and the radial distance from the fixture axis to a thread bottom is $R_{b1}$, and in the trailing portion of the second fixture, the radial distance from the fixture axis to a thread top is $R_{t2}$ and the radial distance from the fixture axis to a thread bottom is $R_{b2}$, wherein $R_{t1}$ is different from $R_{t2}$, and/or $R_{b1}$ is different from $R_{b2}$.

Thus, it should be understood that the applied pressure resulting in the strain in the bone, can be provided by the radial distance to a thread top being increased in the trailing portion compared to the leading portion of a fixture, or by the radial distance to a thread bottom being increased in the trailing portion compared to the leading portion of a fixture (or a combination of both the thread top and thread bottom). Accordingly, by having a larger relative increase in radial distance to thread top and/or thread bottom in the trailing portion in one of the fixtures, that fixture will provide a larger strain to the bone tissue compared to the other fixture or other fixtures in the set.

Although the leading portion of the at least two fixtures in the set may suitably have substantially the same dimensions, while the trailing portions have different dimensions, it would be conceivable to have different dimensions on the leading portions as well.

According to at least one example embodiment, the threading of the leading portion is provided with at least one cutting means/cutting edge for making a female thread in the bone tissue, wherein, in the leading portion of the first fixture the largest radial distance from the fixture axis to a thread top of said cutting edge is $r_{t1}$ and the largest radial distance from the fixture axis to a thread bottom of said cutting edge is $r_{b1}$, wherein, in the leading portion of the second fixture the largest radial distance from the fixture axis to a thread top of said cutting edge is $r_{t2}$ and the largest radial distance from the fixture axis to a thread bottom of said cutting edge is $r_{b2}$, wherein the relationship $$\frac{R_{t1}-r_{t1}}{r_{t1}}$$

is different from the relationship $$\frac{R_{t2}-r_{t2}}{r_{t2}},$$

and/or the relationship $$\frac{R_{b1}-r_{b1}}{r_{b1}}$$

is different from the relationship $$\frac{R_{b2}-r_{b2}}{r_{b2}}.$$

When the cutting edges of the leading portion make a female thread in the bone there will be substantially no strain, since bone is cut away rather than pressed away. When the threaded trailing portion enters the female thread in the bone, due to the increased diameter of the trailing portion, its threads will press the bone in the radial direction creating a static strain in the bone tissue.

In the above embodiment, it does not matter whether it is the trailing or the leading portion which is different in the first fixture compared to the corresponding portion in the second fixture. The difference in strains provided by the two fixtures is dependent on the difference in relative radial increase. However, it may be suitable within one set to have the same radial distance to thread tops and/or thread bottoms in each fixture. Thus, according to at least one example embodiment, $r_{t1}=r_{t2}$ and/or $r_{b1}=r_{b2}$.

According to at least one example embodiment, each one of said fixtures in the set comprises an intermediate transition portion having an apical end which borders to the leading portion and a coronal end which borders to the trailing portion.

The transition portion is provided for achieving the increased diameter, i.e. to widen the fixture from the leading portion to the trailing portion. The transition portion may be threaded. However, alternatively, it may be non-threaded. The function of the transition portion can be regarded as to radially displace the thread tops and/or thread bottoms. With regard to thread tops the transition portion widens the fixture having said radial distance $r_{t1}$ or $r_{t2}$ (fixture axis to thread top in leading portion) to having said radial distance $R_{t1}$ or $R_{t2}$ (fixture axis to thread top in trailing portion). Similarly, with regard to thread bottoms the transition portion widens the fixture from having said radial distance $r_{b1}$ or $r_{b2}$ (fixture axis to thread bottom in leading portion) to having said radial distance $R_{b1}$ or $R_{b2}$ (fixture axis to thread bottom in trailing portion). The axial length of the transition portion is L. Thus, in case of linearly increasing the diameter with respect to the thread tops, the widening per axial unit length caused by the transition portion is $$\frac{R_{ti} - r_{ti}}{L}$$

for the i:th fixture in the set, i=1, 2, . . . . Similarly, in case of linearly increasing the diameter with respect to the thread bottoms, the widening per axial unit length caused by the transition portion is $$\frac{R_{bi} - r_{bi}}{L}.$$

However, the widening of the transition portion does not have to be linear, it may alternatively be non-linear. For instance the transition portion may widen in a curved manner, such as with a convex or concave curvature.

It should be understood that said radial distances $r_t$ and $r_b$ defined by the thread top and thread bottom, respectively, provided with a cutting edge are present in the leading portion. Any axial section of the fixtures having larger radial distances from a fixture axis to thread top/bottom than $r_{ti}/r_{bi}$ is instead part of the transition portion or the trailing portion.

The trailing portion may suitably be cylindrical in order to provide a foreseeable static strain to the bone. However, alternatively, the trailing portion may be slightly widening in the coronal direction in order to compensate for any grinding effect caused by the threads rotating in the bone. In case of a coronally widened trailing portion, such a widening per axial unit length should not exceed the above described widening of the transition portion. Therefore, for a coronally widened trailing portion, the radial distance from the fixture axis to a first thread top may be a first radial distance, and the radial distance from the fixture axis to a second thread top may be a second radial distance. The first and second thread tops are separated by an axial distance. Thus, for the i:th fixture, when taking the difference between the second and the first radial distance, and dividing said difference with said separating axial distance, the result must not exceed $$\frac{R_{ti} - r_{ti}}{L}.$$

The corresponding condition applies when comparing thread bottoms in the trailing portion, i.e. their radial increase per axial unit length must not exceed $$\frac{R_{bi} - r_{bi}}{L}.$$

Thus, it should be understood that while the function of the transition portion is to widen the implant so as to reach a suitable strain level, the function of the trailing portion is primarily to maintain that pressure. Therefore, any widening of the trailing portion should, suitably, only compensate for grinding effects and not to further increase the strain on the bone. Although, the transition portion has been stated to have an axial length L in all the fixtures in the set, an alternative would be to have different lengths $L_i$ of the transition portions in one or more of the fixtures in the set.

It should be understood that the transition portion does not necessarily have to be conically widened in the coronal direction (i.e. conically tapered in the apical direction), but can have other alternative shapes. For instance, according to at least one example embodiment, the coronal widening of the transition portion presents a concave or convex shape.

Also, the trailing portion may have alternative shapes. According to at least one example embodiment, the trailing portion is substantially cylindrical. According to at least one example embodiment, the trailing portion is tapering. According to at least one example embodiment, a coronal part of the trailing portion is cylindrical while an apical part thereof is tapering, or vice versa.

According to at least one example embodiment, both of said fixtures in the set are externally threaded, wherein the axial length of the threading of the first fixture is substantially the same as the axial length of the threading of the second fixture. Thus, the set of fixtures may include fixtures having substantially the same overall axial lengths, or at least substantially the same axial length of the threading. However, although the overall axial length or axial length of the threading is the same throughout the set of fixtures, certain portions may be differently dimensioned, e.g. trailing or condensation portions which have different widths on different fixtures.

According to at least one example embodiment, each one of said fixtures comprises a leading portion and a wider trailing portion for providing the static strain to the bone tissue, wherein the axial length of the trailing portion of the first fixture is longer than the axial length of the trailing portion of the second fixture, whereby the static strain in the bone is applied over a longer axial distance if the first fixture is installed compared to if the second fixture is installed. Thus, while the axial extent of the strain on the bone tissue will be different depending on which fixture is used, the magnitude of the strain may, as such, be the same regardless of which fixture is used. Alternatively, also the magnitude of the strain may vary from fixture to fixture.

Accompanying FIG. 1 is an illustration of the relationship between stress and strain in the cortical bone tissue. The yield point is at the transition between the straight part (elastic deformation zone) and curved part (plastic deformation zone) of the graph. The ultimate strain is at the other end of the curved part.

Accompanying FIG. 2 is an illustration of the relationship between stress and strain in cancellous bone tissue. For cancellous bone, the behavior up to the yield point (i.e. where the straight part of the graph transits into the curved part) substantially corresponds to that in cortical bone. However, as may be seen from FIG. 2, the behavior above the yield point differs somewhat between cancellous bone and cortical bone.

It should be noted that the graphs in FIG. 1 and FIG. 2 illustrate the absolute values of the stresses and strains.

In this application, when strain is discussed, or when different values of strain are discussed, unless explicitly specified, the discussion may relate to tensile strain and/or compressive strain. All strain-related numbers are presented in absolute values.

The inventors have realized that a static strain in bone in the range of 0.01-0.3 (absolute values) provides a good bone strength during the healing phase, i.e. above the yield strain (for a normal 70 year old patient the yield strain of cortical bone may be below 0.01).

Thus, according to at least one example embodiment, the static strains provided by said fixtures are in the range of 0.01-0.3. For instance, in a set of fixtures, a first fixture may provide a strain of 0.01, a second fixture may provide a strain of 0.02, a third fixture may provide a strain of 0.03, etc.

Since this static strain may be achieved, e.g. by means of an increased width of the fixtures, according to at least one example embodiment, each fixture comprises a threaded leading or cutting portion in which the threading is provided with at least one cutting edge for making a female thread in the bone tissue, wherein the largest radial distance from the fixture axis to a thread top of said cutting edge is $r_{ti}$ (index i stands for the i:th implant, i=1, 2, . . . ) and the largest radial distance from the fixture axis to a thread bottom of said cutting edge is $r_{bi}$, a threaded trailing or condensation portion in which the smallest radial distance from the fixture axis to a thread top is $R_{ti}$ and the smallest radial distance from the fixture axis to a thread bottom is $R_{bi}$, wherein at least one of the ratios $$\frac{R_{ti} - r_{ti}}{r_{ti}} \text{ and } \frac{R_{bi} - r_{bi}}{r_{bi}}$$

is in the range of 0.01-0.3.

In particular, the inventors have identified that the lower part of the range is suitable for cortical bone, while the upper part of the range is suitable for spongious cancellous bone.

Thus, according to at least one example embodiment, at least for one or more (or all) of the fixtures in the set, the above ratios or strains are in the range of 0.01-0.1, such as in the range of 0.01-0.03, suitably in the range of 0.01-0.02.

The strain range of 0.01-0.02 is normally between the yield strain and ultimate strain of human cortical bone. However, as mentioned previously, even with strains exceeding the ultimate strain of human cortical bone, beneficial effects may be accomplished. Of course, for cancellous bone, considerably higher strains may be applied to the bone, since in cancellous bone the yield strain and ultimate strain are much higher than for cortical bone. This is reflected in at least one example embodiment in which at least one of the ratios $$\frac{R_{ti} - r_{ti}}{r_{ti}} \text{ and } \frac{R_{bi} - r_{bi}}{r_{bi}}$$

is in the range of 0.06-0.3, suitably in the range of 0.06-0.1, for at least one or more (or all) of the fixtures in the set. While the narrower range may still be suitable for use in cortical bone, the wider range is also suitable for cancellous bone.

According to at least one example embodiment, the axial length of the threading of the trailing portion is about 0.5-4 mm, suitably 1-3 mm. Such axial length substantially corresponds to normal thickness of cortical bone. Thus, fixtures according to such an embodiment, are particularly suitable for applying a static strain to the cortical bone. Therefore, suitably, the trailing portion is a coronal end portion of the bone apposition surface of the fixture.

According to at least one example embodiment, the axial length of the threading of the trailing portion is greater than 1 mm, such as greater than 3 mm, suitably greater than 4 mm. Fixtures according to such an embodiment are suitable for cancellous bone, which is located below the cortical bone. Thus, the axial length should be large enough to reach through the cortical bone and down to the cancellous bone. Suitably, for such an installation of a fixture, the bore hole at the cortical bone may be countersunk, i.e. widened, in order to avoid too high strain provided by the trailing portion on the cortical bone. This will allow a high strain to be applied to the cancellous bone, without providing the same high strain to the cortical bone.

Suitably, in the trailing portion, not only the thread top(s) and/or thread bottom(s) having the smallest radial distance to the fixture axis are dimensioned to provide said strain ranges, but also the other thread tops and/or thread bottoms of the trailing portion are so dimensioned. This is reflected in at least one example embodiment, according to which in the trailing portion the largest radial distance from the fixture axis to a thread top and the largest radial distance from the fixture axis to a thread bottom is dimensioned so that the ratios are in the range of 0.01-0.3, suitably in the range of 0.01-0.1, such as in the range of 0.01-0.03, suitably in the range of 0.01-0.02.

Although in at least one example embodiment, the fixtures of the set do not comprise any other threaded portions, in other example embodiments the fixtures may, for instance, comprise one or more threaded portions, such as coronally of the trailing portion.

According to at least one example embodiment, each one of said fixtures comprises an apical cutting portion for cutting a female thread into the bone tissue, an apical condensation portion for providing a static strain to the bone tissue and being located coronally of the apical cutting portion, a coronal cutting portion for cutting a female thread into the bone tissue and being located coronally of the apical condensation portion, a coronal condensation portion for providing a static strain to the bone tissue and being located coronally of the coronal cutting portion, wherein at least one of said cutting portions and condensation portions of the first fixture has a different width with respect to major and/or minor fixture diameter compared to the corresponding portion of the second fixture.

The cutting portion may correspond to the previously discussed leading portion. Similarly, the condensation portion has the function of the previously discussed trailing portion.

Thus, two axially separated locations of tensile strain may be provided to the bone with a fixture having along its axis an additional portion for cutting threads in the bone, and additional trailing/condensation portion. Thus, the widening of the implant at the transition from the apical cutting portion to the apical condensation portion enables the apical condensation portion to provide a first tensile strain to the bone, while the widening of the implant provided by the coronal portions enable the coronal condensation portion to provide a second tensile strain to the bone. Although, said first and second tensile strains may have the same value, it may be advantageous to have different values. For instance, the fixture may be designed so that said first tensile strain will substantially be provided to the cancellous bone while the second tensile strain will be substantially provided to the cortical bone. In such case, since the ultimate strain of the cancellous bone is higher than the ultimate strain of the cortical bone, the applied first tensile strain may suitably be higher than the second applied tensile strain.

Within the set, different fixtures may be arranged to provide e.g. different tensile strains by the coronal condensation portion, or by the apical condensation portions, or by both the coronal condensation and apical condensation portions. Thus, since each fixture in the set according to this embodiment may be arranged to provide tensile strains to two axially different areas of the bone tissue, and the various portions may be designed differently for each fixture, a set of fixtures may be provided with numerous alternatives for a dentist/surgeon to choose from based on the particular patient.

The inventive set of fixtures may be applicable to different parts of the human bone tissue. According to at least one example embodiment, said fixtures are dental fixtures for arrangement in jawbone.

Apart from the example embodiments described above, for one or more (or all) of the fixtures in the set, there are also some other example embodiments which will be presented below. Reference will be made to a fixture (i.e. singular), but it should be understood that other fixtures within the set may also have the presented features.

According to at least one example embodiment, the threads in the trailing portion are microthreads. In an alternative embodiment, only parts of the threads in the trailing portion are microthreads. In yet an alternative embodiment, the threads in the trailing portion are macrothreads.

According to at least one example embodiment, at least a coronal portion of the transition portion is provided with microthreads which are continuous with microthreads in the trailing portion. In at least one alternative embodiment, the entire threading of the transition portion is in the form of microthreads. According to at least one additional or alternative example embodiment, at least a coronal portion of the leading portion is provided with microthreads.

According to at least one example embodiment, the trailing portion is conically widened in the coronal direction. This may be suitable in order to compensate for any grinding effect on the bone caused by the threading during insertion.

According to at least one example embodiment, the threads in the trailing portion have the same thread profile as the threads in the leading portion. Thus, in at least one example embodiment the thread profile along the threaded portions is constant. According to an alternative example embodiment, the threads in the trailing portion have a larger thread profile compared to the profile of the threads in the leading portion. A thread profile comprises two flanks, a top interconnecting said two flanks, a bottom formed between two adjacent threads, said flanks forming an angle with a plane which is perpendicular to the fixture axis and which angle lies in a plane containing the extension of the fixture axis, said profile further having a height. Said top may have a top radius and said bottom may have a bottom radius.

According to at least one example embodiment, the threads in the trailing portion have the same thread profile as the profile of the threads in the transition portion and/or the leading portion. According to at least one example embodiment, said thread profile is a microthread profile. According to at least one example embodiment, the threads in the trailing portion are microthreads having substantially the same profile as the outermost part of the threads in the transition portion and/or the leading portion.

By having a constant or substantially constant thread profile throughout the different portions, the radial pressure caused by the trailing portion can be effectively controlled. In other words, with regard to the fixture axis, the thread profile may simply be subject to parallel displacement in the radial direction when comparing the leading portion and the trailing portion.

According to at least one example embodiment, the threads in the trailing portion, the transition portion and the leading portion have the same top radius and flank angles. For instance, even though the threads in the leading portion may at least partially be provided with macrothreads, while the trailing portion may be provided with microthreads, thus having different thread height, because of the same top radius and flank angles, the profile/contour of a microthread which follows the path of the macrothread will fit the profile/contour of the female bone threads created by the macrothreads. Thereby, the bone is well supported also by the microthread. Suitably, part of the leading portion may be provided with microthreads having a cutting edge for making female threads in the bone.

According to a second aspect of the invention, an implantation system is provided. The system comprises an externally threaded fixture for insertion into a bore hole arranged in bone tissue, the fixture having a leading portion and a wider trailing portion, a first separate externally threaded thread maker having at least one cutting edge for making a female thread in the bone tissue, which female thread is adapted to mate with the thread of the fixture, a second separate externally threaded thread maker having at least one cutting edge for making a female thread in the bone tissue, which female thread is adapted to mate with the thread of the fixture, wherein, in the first thread maker, the largest radial distance from the
centre axis to a thread top and/or thread bottom of said cutting edge is different from the largest radial distance from the centre axis to a thread top and/or thread bottom, respectively, of the cutting edge of the second thread maker.

The threads of the thread makers should suitably have the same lead as the threads of the fixture. In connection with the first aspect of the invention, it was described that to create the tensile strain in the bone tissue, a female thread is cut into the bone and when a wider/overdimensioned trailing/condensation portion passes in the female thread a pressure will be applied to the bone tissue and tensile strain arises. In the first aspect it was described that the fixtures have cutting edges for cutting female threads in the bone. In the second aspect, a separate thread maker is used instead. This enable a dentist/surgeon to just have one type of fixture, and when selecting a suitable strain, he/she simply selects which one of the thread makers to use. Since each thread maker creates female threads with different depths, the pressure, and thus the strain, caused by the trailing/condensation portion of the fixture will depend on the selected thread maker.

According to at least one example embodiment of the implantation system, said female thread in the bone tissue made by either one of the first or second thread makers has a first portion for receiving the leading portion of the fixture and a second portion for receiving the trailing portion of the fixture, wherein, with respect to major and/or minor fixture diameter and corresponding major and/or minor bore diameter, the diametrical difference between the leading portion and said first portion is smaller than the diametrical difference between the trailing portion and said second portion, whereby the trailing portion provides a static strain to the bone tissue. Thus, the trailing portion of the fixture may have the same major diameter as the leading portion of the fixture, but a larger minor diameter. Alternatively, the trailing portion has a larger major diameter, but not a larger minor diameter, compared to the leading portion. Yet an alternative, is to provide a trailing portion with both the major and minor diameters larger than those of the leading portion. Since the diametrical difference between the trailing portion of the fixture and the receiving second portion of the female bone thread is larger than the diametrical difference between the leading portion of the fixture and the receiving first portion of the female bone thread, the trailing portion will provide a larger pressure to the bone than the pressure (if any) provided by the leading portion. Although the diametrical difference between the leading portion of the fixture and the receiving first portion of the female bone thread may be a non-zero value, it is indeed conceivable to have a zero difference.

With respect to the above, it would for instance be conceivable to make a cylindrical bore hole and then select one of at least two thread makers, each one having cutting edge with a different cutting depth. As an example one of the thread makers may provide a female thread having substantially the same major diameter as that of the leading portion of the fixture, wherein only the wider trailing portion will act to condense the bone tissue. Another thread maker may provide a female thread having slightly smaller major diameter compared to the leading portion of the fixture, wherein the leading portion will cause a slight condensation of the bone and the wider trailing portion will cause a larger condensation of the bone.

According to at least a third aspect of the invention, there is provided a method of selecting a fixture from a set of at least two fixtures, each fixture, compared with the other fixture or fixtures, being adapted to provide a different static strain if inserted into a bore hole in the bone tissue of a person, the method comprising:
  determining the state or value of a strain-affecting characteristic of a person or a person's bone tissue, and
  selecting a fixture from said set based on the determined state or value.

The fixture may have any one or more of the features of the fixtures presented in connection with the disclosure of the first aspect of the invention. It should be understood that the determination of the state or value of a strain-affecting characteristic of a person or a person's bone tissue, can be performed non-invasively.

According to at least one example embodiment, said strain-affecting characteristic is one of: the person's age, bone density, mineral content of the bone tissue, bone tissue disease and bone thickness.

As regards, a person's age, McCalden R. W. et al. (*Age-related changes in the tensile properties of cortical bone*, The Journal of Bone and Joint Surgery, Vol. 75-A. No. 8, August 1993) showed that the ultimate strain for younger persons is higher than that of older person. Thus, a suitable strain to be applied to the bone of a 20-year old person may be much higher than a suitable strain to be applied to the bone of an 80-year old person. Thus, a dentist/surgeon may decide to choose a fixture from the set which provides a higher strain if the patient is younger and a fixture which provides a lower strain if the patient is older.

The bone density can be analyzed, for instance, by means of dual-energy X-ray absorptiometry, single-photon absorptiometry or computer tomography.

The yield and ultimate strain of the bone is reduced if the mineral content is increased. Thus, for a patient having a high mineral content in the bone, a fixture should be chosen which provides a lower strain than a fixture which would be chosen for a patient having a lower mineral content. The mineral content of the bone tissue may, for instance, be analyzed by means of ultrasound or computer tomography.

Different bone tissue diseases affect the yield and/or ultimate strain of the bone tissue. According to Cowin, S (Bone Mechanics Handbook, second edition, Informa Health Care, 2009, pp 12-1-12-3) diseases that interfere with the ability of mineral ions to be deposited within the collagen "scaffold" yields bones that bend, but do not necessarily break. These diseases are usually diagnosed as "rickets" in the growing skeleton and as "osteomalacia" in the adult one. Diseases in which either the structure or the quantity of collagen fibres is "abnormal" produce brittle bones and fall under the category of "osteogenesis imperfect".

Bone thickness may be analyzed by means of, for instance, X-ray.

The fixtures discussed in the various aspects and embodiments of the invention, may be dental fixtures. Such a dental fixture may be comprised in a dental implant. A dental implant may, in addition to the dental fixture, also comprise a superstructure, such as an abutment.

The dental fixture is for use as the anchoring member of a dental prosthesis. To this end, the dental fixture is insertable into a pre-prepared bore hole in the bone tissue of a jawbone (maxilla or mandible) at a site where the dental prosthesis is required. The dental fixture is normally rotated into the bore hole.

The dental fixture is a screw-type dental fixture. To this end the bore hole may be provided with internal (female) threads, in advance or may be left un-tapped with the dental fixture provided with a self-tapping capacity, e.g. by the provision of one or more axially-extending cutting recesses, edges or notches, etc in the fixture thread. For instance, an apical end portion of the fixture may be provided with 2-4 cutting recesses, such as 3 cutting recesses. Other number of cutting recesses are readily conceivable.

A superstructure for connecting a prosthetic part to the fixture may comprise an abutment, spacer or other transmucosal component which engages to the dental fixture to bridge the gingiva overlying the maxilla or mandible. The prosthetic part, e.g. a crown, bridge or denture may be secured to the abutment. There are various other forms that the superstructure can take. For instance, the prosthetic part may be secured directly to the dental fixture. A dental implant may thus comprise an abutment connected to the dental fixture, or the dental fixture without an abutment.

The term "coronal" is here and throughout this application used to indicate a direction towards a head end or trailing end of the dental implant. For instance, in a situation where an abutment is connected to a dental fixture, the coronal direction of the abutment would be a direction towards the part of the abutment being directed away from the fixture. Conversely, the term "apical" indicates a direction towards an insertion or leading end of the component. Thus, apical and coronal are opposite directions. Furthermore, the terms "axial", "axial direction" or "axially" are used throughout this application to indicate a direction taken from the coronal end to the apical end, or vice versa. The terms "radial", "radial distance" or "radially" indicate a direction perpendicular to the axial direction.

A blind bore or socket may extend apically into the fixture body from the coronal end to an end surface in-between the apical and coronal ends of the fixture body for a superstructure to be secured to the fixture. The socket may comprise an internally-threaded section for screw connection of the superstructure to the fixture. A rotational lock for the superstructure may be provided in the socket, such as an internal polygonal side wall, e.g. hexagonal, or alternatively one or more protrusions from or indentations in the wall of the socket. A section of the socket, such as the coronal section, may be tapered towards the apical end. The tapered section is suitably arranged coronally of the internally-threaded section.

The fixture may be used in a one stage procedure or a two stage procedure. In a one stage procedure a healing or temporary abutment is connected to the fixture to form the gingival tissue, and after a healing period the healing or temporary abutment is replaced by a permanent abutment. For a two stage procedure the fixture is provided with a cover screw and the gingival tissue is sutured over the fixture and cover screw, and after a healing period the tissue is opened up and an abutment is connected to the fixture after removal of the cover screw.

A conceivable alternative to having an abutment connected to the fixture is to have a one-piece implant, wherein a portion of the implant is embedded in bone tissue, while another portion of the implant extends from the bone tissue across the gingiva.

The fixture may have a conically tapering end portion which tapers towards the coronal end. The axial extent of this coronal end portion is small compared to the total length of the fixture, as an example no more than 4% of the total length, such as in the range of 1.5%-3.7%. The coronal end portion may suitably be provided without a threaded surface, e.g. having a smooth or a roughened (such as blasted) surface.

The fixture may have a substantially flat coronal end surface which is perpendicular to the longitudinal axis of the fixture. Alternatively, the coronal end surface may have a sloped contour relative to the longitudinal axis of the fixture, e.g. such that when positioned within the jawbone the length of the fixture is larger on a lingual side and shorter on a buccal side of the fixture. Another alternative is a saddle-shaped or wave-like coronal end surface.

The length of the dental fixture may be in the range of 5-19 mm, depending on the clinical situation. The outer diameter of the dental fixture may suitably be in the range of 2-6 mm, such as 3-5 mm.

The fixture may be substantially cylindrical or slightly tapering from the coronal end towards the apical end. If the fixture has a slight tapering, the core of the fixture and the outer periphery defined by e.g. thread tops may have the same or different angle of taper. Furthermore, the core of the fixture may be cylindrical while the thread tops describe a conicity or, conversely, the core of the fixture may be tapered while the thread tops describe a generally cylindrical geometry. Alternatively, the fixture may comprise a combination of one or more cylindrical and/or one or more tapering portions. Thus, one or more portions of the fixture may have e.g. thread tops lying in a common imaginary cylindrical surface, which cylindrical surface is parallel with the longitudinal axis of the fixture. Alternatively or additionally, one or more portions of the fixture may have thread tops lying in an imaginary conical surface which in the apical direction is tapering towards the longitudinal axis.

The externally threaded fixture may comprise one or more thread spirals.

The term "pitch" is used to indicate the axial distance between adjacent tops of a threading. The term "lead" is used to indicate the distance advanced parallel to the longitudinal axis when the fixture is turned one revolution, i.e. it corresponds to the pitch multiplied with the number of thread spirals. For a single thread spiral having a constant pitch, the lead is equal to the pitch; for a double thread spiral, the lead is twice the pitch.

The term "microthread" is used to indicate a thread having a height which is no greater than 0.2 mm. According to at least one example embodiment, the fixture is provided with microthreads having a height in the range of 0.02-0.2 mm, such as 0.05-0.015 mm, for instance 0.1 mm. The term "macrothread" is used to indicate a thread having a height which is greater than 0.2 mm. According to at least one example embodiment, the fixture is provided with macrothreads having a height in the range of 0.25-0.35 mm, such as 0.3 mm.

Suitably, microthreads may be located coronally of macrothreads. For instance, microthreads may be arranged to engage dense cortical bone and macrothreads may be arranged to engage porous spongious/cancellous bone. The lead of a microthread suitably corresponds to the lead of a macrothread. The macrothread pitch may, as an example, be 2-4 times, such as 3 times, the pitch of the microthreads. The pitch (top-to-top spacing) at a fixture portion provided with microthreads may be around 0.10-0.30 mm, for instance 0.20-0.24 mm. The pitch (top-to-top spacing) at a fixture portion provided with macrothreads may be around 0.30-0.90 mm, for instance 0.60-0.72 mm.

Microthreads can be regarded as defined, oriented roughness. A non-oriented roughness having smaller dimensions, for instance obtained by blasting, etching, etc., may be superimposed on microthreads as well as on macrothreads.

A thread profile may comprise two flanks, a top interconnecting said two flanks, a bottom formed between two adjacent threads, said flanks forming an acute angle v with a plane which is perpendicular to the fixture axis and which angle v lies in a plane containing the extension of the fixture axis, said profile further having a height D. The top may be curved and may have a top radius. Suitably, for $10° \leq v < 35°$, the top radius is greater than $0.4 \times D$ and, for $35° \leq v < 55°$, the top radius is greater than $0.2 \times D$.

According to at least one exemplary embodiment, the flanks of the threads have a straight extension.

According to at least one exemplary embodiment, the flanks of the threads have a curved extension. It is for example conceivable with flanks having a concave curvature. It is also conceivable with flanks having a convex curvature.

It should be understood that the basic idea of being able to select from a collection of fixtures a controllable strain to the bone, can in all aspects of the invention, be achieved either by changing the radial distance from fixture axis to the thread tops or by changing the radial distance from fixture axis to the thread bottoms, or by changing both of said radial distances.

BRIEF DESCRIPTION OF THE DRAWINGS

FIG. 4a illustrates a detail of a fixture from a set of fixtures according to at least one example embodiment of the invention.

FIG. 4b illustrates a detail of a fixture from a set of fixtures according to at least one example embodiment of the invention.

FIG. 7c illustrates a set of fixtures according to at least another example embodiment of the invention.

FIG. 7d illustrates a set of fixtures according to at least another example embodiment of the invention.

FIG. 9a illustrates an implantation system according to at least one example embodiment of the invention.

FIG. 9b illustrates an implantation system according to at least one example embodiment of the invention.

FIG. 9c illustrates an implantation system according to at least one example embodiment of the invention.

FIG. 9d illustrates an implantation system according to at least one example embodiment of the invention.

DETAILED DESCRIPTION OF THE DRAWINGS

Figure 1:
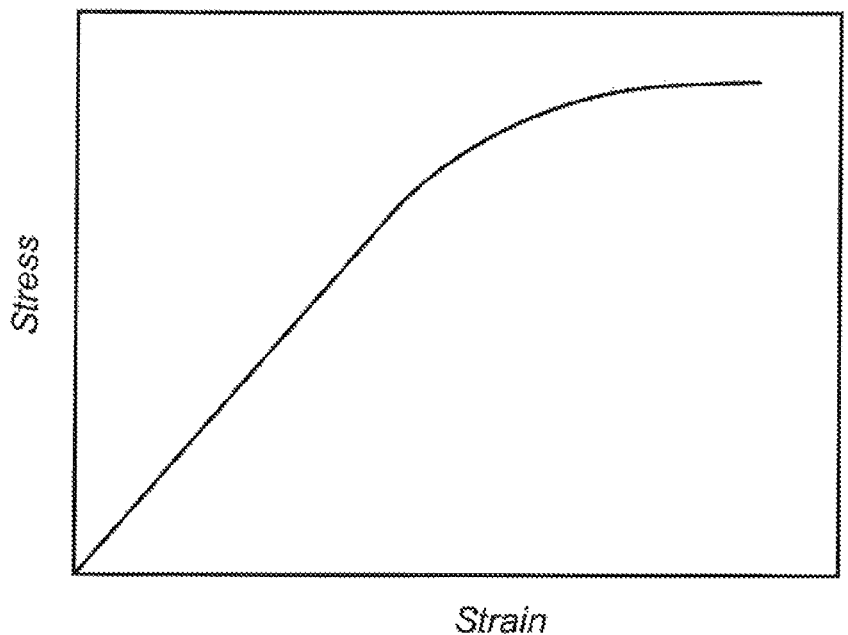
FIG. 1 is a graph illustrating a stress/strain relationship for cortical bone.

FIG. 1 is a graph illustrating a stress/strain relationship for cortical bone. In an article by McCalden R. W. et al. the relationship between ultimate strain and age is presented (McCalden R. W. et al., *Age-related changes in the tensile properties of cortical bone*, The Journal of Bone and Joint Surgery, Vol. 75-A. No. 8, August 1993). From the article, one learns that the ultimate strain is substantially linearly dependent on the person's age. For instance, an 80 year old person has in cortical bone an ultimate strain of about 0.015, a 50 year old person has an ultimate strain of about 0.025, while a 20 year old person has an ultimate strain of about 0.035. For cortical bone the yield strain is about half the ultimate strain. For instance, with reference to FIG. 1, in a 20 year old person, for a strain up to about 0.018, the stress/strain relationship could be linear and represents an elastic deformation of the bone. The interval between 0.018 and 0.035 is non-linear and represents a plastic deformation of the cortical bone. Similarly, for an 80 year old person, a strain up to 0.008 would correspond to the linear relationship and the interval between 0.008 and 0.015 would correspond to the non-linear relationship in FIG. 1.

Example

Screw shaped fixtures, manufactured from commercially pure titanium, grade 4, were used. In order to reduce a possible grinding effect during insertion the fixtures had a turned surface. The endosseous part of the fixtures comprised three different portions; one leading (cutting) portion, one transition portion with a gradual increase in diameter and one trailing (condensation) portion. The bone bed was drilled to a final burr diameter of 3.3 mm corresponding to the core diameter ($2r_b$) of the cutting portion of the fixture. When the fixture was inserted the cutting features created a cavity in the bone which was congruent with the fixture shape of the cutting portion. When the transition portion entered the bone it created a gradual increase in the strains in the surrounding bone without cutting. When finally the condensation portion entered the bone the predetermined bone condensation was obtained. The fixtures were installed with a standardized rotation speed of 20 revolutions/minute. Two types of test fixtures were used; one where the increase in diameter was 0.15 mm (referred to as "Group 0.15") and another with a diameter increase of 0.05 mm (referred to as "Group 0.05"). The control fixtures had no diameter increase.

The fixtures were inserted in tibia of rabbits. Test fixtures were always inserted in the left leg and control fixtures in the right leg. Group 0.15 fixtures were installed proximally in the proximal tibia metaphysis. Group 0.05 fixtures were installed distally in the proximal tibia metaphysis.

After 3.5 weeks, all fixtures were subjected to removal torque (RTQ) tests. The peak RTQ was investigated with a computerized control RTQ device, in which the values were transmitted at a frequency of 100 per second to the computer via a control box.

The fixture head was connected to the instrument, and an increasing reverse torque was applied to all the fixtures until failure of the bone-fixture interface occurred. The first peak values of resistance to reverse torque rotation were recorded in Ncm.

Prior to the animal experiment a 2D axisymmetric finite element model of the trailing portion of the fixture and the surrounding bone was developed. The fixture and the bone were modelled in a CAD software Pro/Engineer (PTC Corporate Needham, Mass. USA) and then transferred into the finite element software ANSYS 12.01 (ANSYS, Inc. Canonsburg, Pa., USA). The strain in the bone was induced by radial displacement of the fixture surface by 0.025 mm and 0.075 mm simulating a diameter increase of 0.05 mm and 0.15 mm respectively. The simulated maximum principal strain in the surrounding bone for Group 0.15 fixtures was ~0.045 (0.15 mm divided by 3.3 mm=0.045). For group 0.05 fixtures the maximum principal strain obtained was ~0.015 (0.05 mm divided by 3.3 mm=0.015).

In all sites the removal torque of the test fixtures was higher than that of the corresponding control fixtures. See Table 1.

TABLE 1

Comparison between removal torque for test fixtures and control fixtures.

| Removal | Average torque Test Ncm (Std) | Average torque Control Ncm (Std) |
|---|---|---|
| Tibia proximal (Group 0.15) | 26.0 (6.89) | 16.8 (7.83) |
| Tibia distal (Group 0.05) | 23.0 (5.31) | 17.2 (5.29) |

Strain in cortical bone from rabbits has been measured by Shunmugasamy V. C. et al. and presented in an article (Shunmugasamy V. C. et al., *High strain rate response of rabbit*

*femur bones*. Journal of Biomechanics, 2010; 43: 3044-3050). The ultimate strain of rabbit cortical bone was measured to be about 0.02.

In the present study the fixtures were just supported by cortical bone. It should be noted that the Group 0.15 fixtures gave rise to strains (0.045) which exceeded the ultimate strain (~0.02) of cortical rabbit bone. In spite of this there was no evidence of reduced removal torque. On the contrary the removal torque of the experimental fixtures was higher than that of the control fixtures which were designed not to produce static strains in the bone. It is striking that the very highest removal torque was obtained for Group 0.15 fixtures for which the strains induced by far exceeded the ultimate strains. From the values in Table 1, one can simply calculate that for Group 0.15 fixtures the removal torque was increased by 55%, and for Group 0.05 fixtures the removal torque was increased by 34%. Obviously, the stresses in the bone, which were induced during fixture insertion, are maintained for a considerable time.

This study indicates that an increased strain provides better initial fixture stability, it is also noticeable that increased strain provides a better stability after 3.5 weeks.

In the above-mentioned article by McCalden R. W one learns that the ultimate strain is substantially linearly dependent on the person's age. The above discussed ultimate strain (~0.02 of rabbits) can be seen for a 70 year old person. While the rabbit experiments in the above discussed example showed a successful result for a strain of 0.045, which by far exceeds the ultimate strain of cortical rabbit bone (2¼ times the ultimate strain of cortical rabbit bone), and also exceeds the ultimate strain of cortical bone of a 70 year old human, it is anticipated that an even higher strain would be successful in a younger person's cortical bone. For a 20 year old person, it would correspond to applying a strain of about 0.08 (2¼ times the ultimate strain 0.035 of a 20 year old person). For a child or adolescent the ultimate strain is even higher, for instance 0.04, which means that a strain of 0.09 could be applied. The rabbit study in the above example did not measure the upper limit for suitable static radial strain, but since the Group 0.15 fixtures surprisingly provided an even better result than the 0.05 fixture, it is reasonable to assume that even higher strains relative to the ultimate strain may be suitable for cortical bone.

While the above study analyzed the strain in cortical bone, an analogy may be made to strains in cancellous bone. Thus, similarly to the previous explanations with regard to providing a tensile strain in cortical bone above the yield strain, a beneficial biological response may also be triggered by providing a tensile strain in cancellous bone above the yield strain of the cancellous bone.

Figure 2:
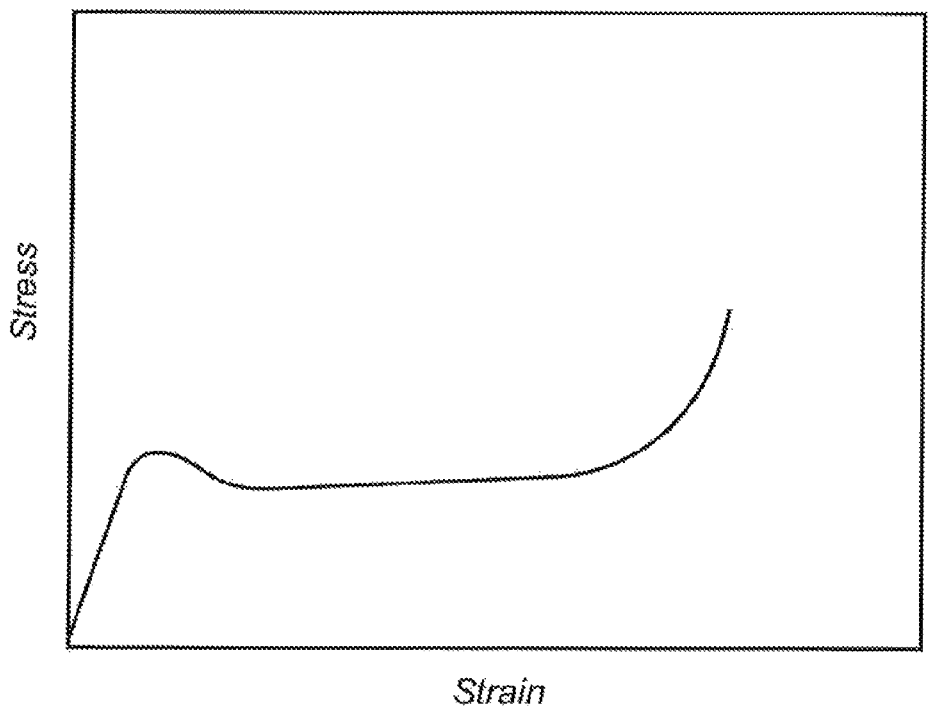
FIG. 2 is a graph illustrating a stress/strain relationship for cancellous bone.

FIG. 2 is a graph illustrating a stress/strain relationship for cancellous bone. The behavior of the graph up to the yield point is similar to that of FIG. 1, i.e. a linear relationship is presented. However, the curved part above the yield point is different and more stretched. According to Gibson, the yield strain is about 0.06 for cancellous bone (Gibson, J. Biomechanics, Vol. 18, No. 5, pp 317-328, 1985). Drawing conclusions from an article by Kold S. et al. (Kold S. et al., *Compacted cancellous bone has a spring-back effect*. Acta Orthopaedica Scandinavica, 2003; 74(5): 591-595) the yield strain for cancellous bone may be even higher. According to Kold S. et al. a bore hole of 5.0 mm in diameter was made in cancellous bone. The bone was then compacted by expanding the bore to 5.6 mm, after which the bone sprung back. During the compaction, the tensile strain ΔDD on the cancellous bone was therefore 0.6/5=0.12. Thus, the yield strain in cancellous bone is multiple that of the yield strain in cortical bone. In addition, the plastic deformation of cancellous bone is much more stretched than for cortical bone. Thus, since a strain level of 0.1 is considered by the inventors to be suitable for cortical bone tissue, at least for some age groups, a strain level of 0.3 should be suitable for cancellous bone tissue.

Figure 3A:
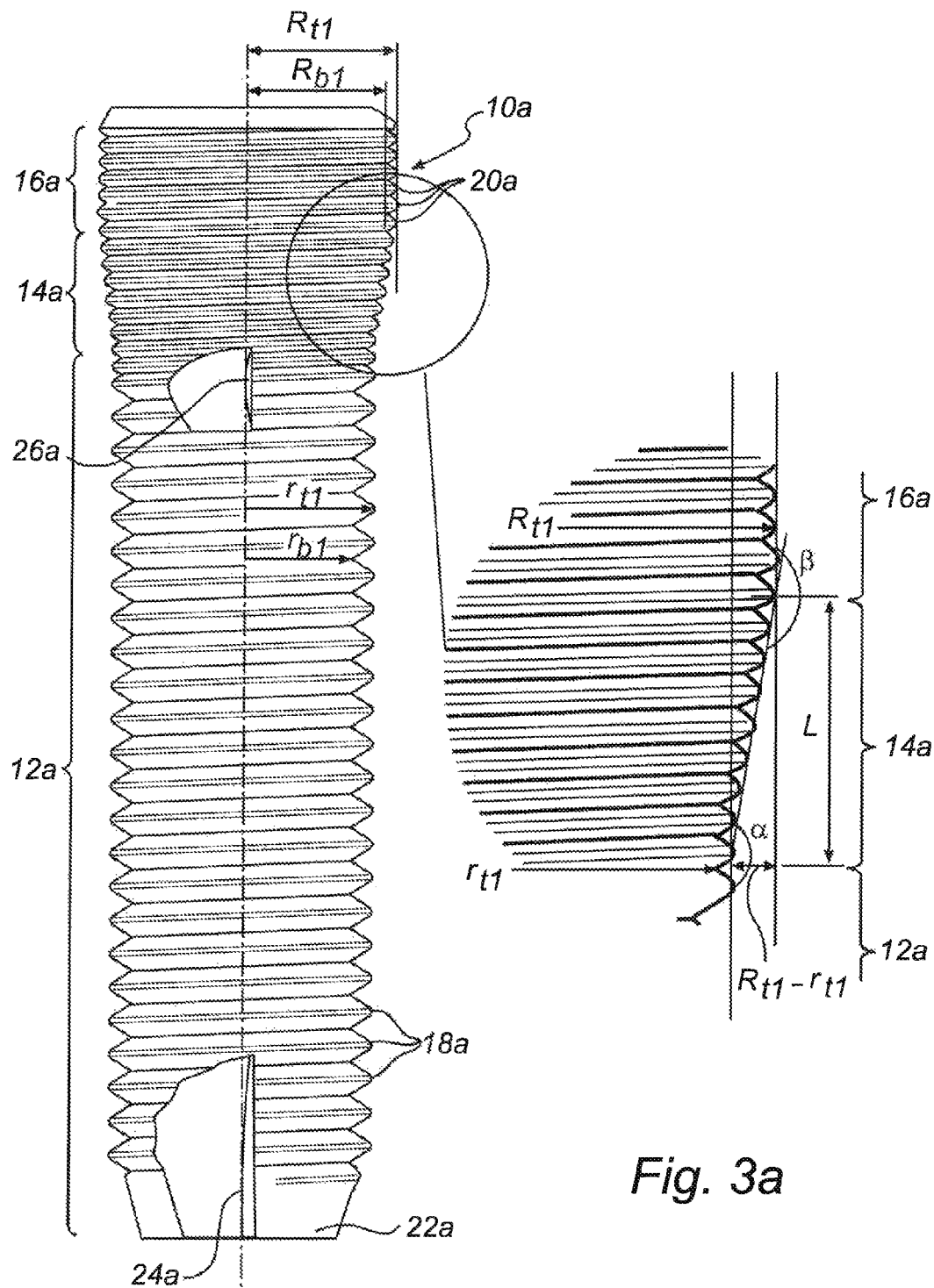
FIG. 3a illustrates a set of fixtures according to at least one example embodiment of the invention.
Figure 3B:
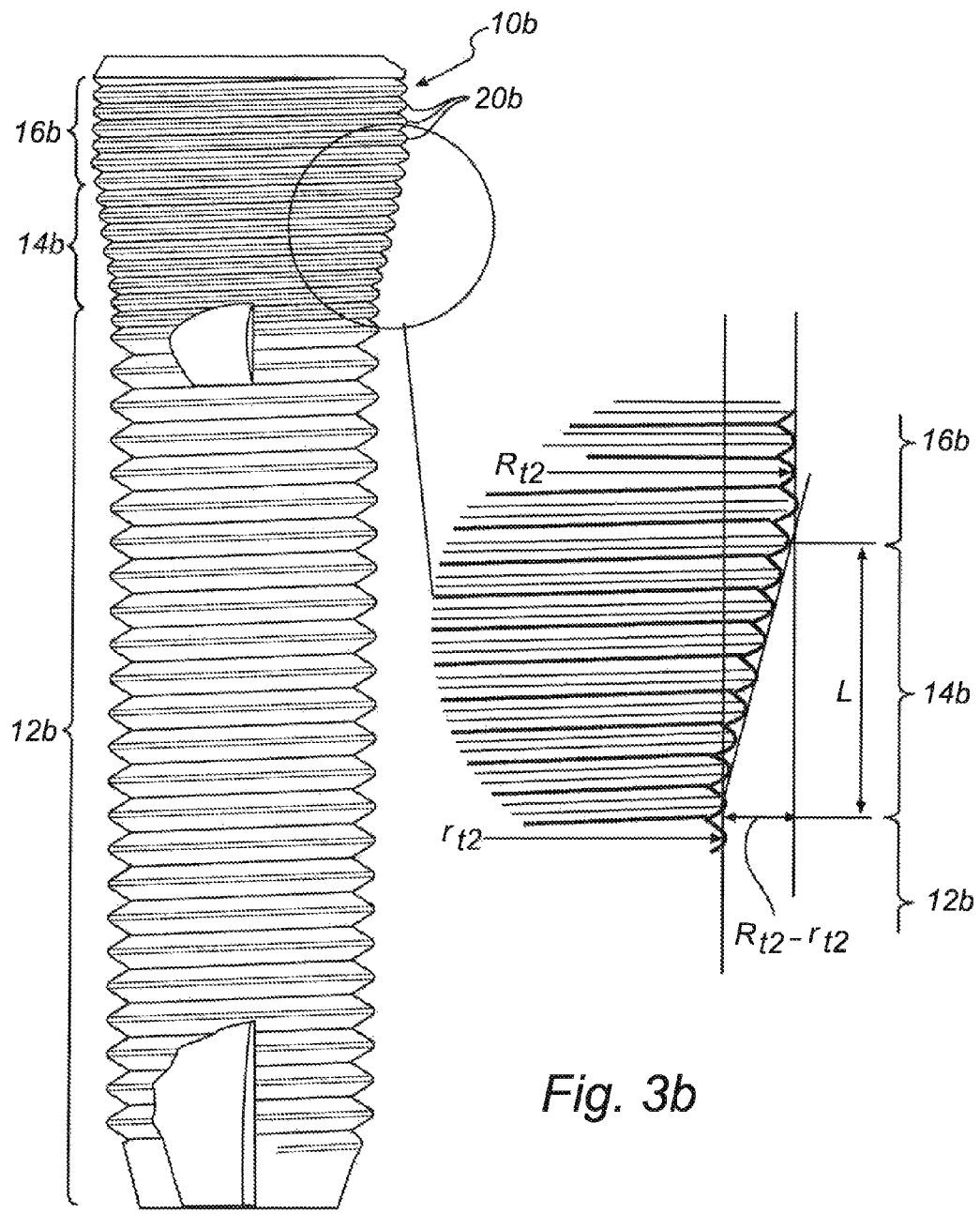
FIG. 3b illustrates a set of fixtures according to at least one example embodiment of the invention.

FIGS. 3a-3b illustrate a set of fixtures according to at least one example embodiment of the invention. The set of fixtures comprises a first fixture 10a illustrated in FIG. 3a and a second fixture 10b illustrated in FIG. 3b.

With reference to FIG. 3a, the first fixture comprises a leading portion 12a, a transition portion 14a located coronally of the leading portion 12a, and a trailing portion 16a located coronally of both the leading portion 12a and the transition portion 14a. Each one of said portions present a respective outer surface being threaded for engagement with bone tissue, wherein thread tops and thread bottoms are provided alternatingly in the axial direction of the fixture.

In the illustrated example, the leading portion 12a is provided with macrothreads 18a while the transition 14a and trailing portions 16a are provided with microthreads 20a. An alternative would be to provide at least a coronal subportion of the leading portion 12a with microthreads. Alternatively, all three portions could be provided with macrothreads.

The outer surface of the leading portion 12a forms an angle α of less than 180° in relation to the outer surface of the transition portion 14a (see the enlarged detailed view), and wherein the outer surface of the transition portion 14a forms an angle β of greater than 180° in relation to the outer surface of the trailing portion 16a. While the enlarged detailed view in FIG. 3a shows that the thread tops form said angular relationship of said outer surfaces, it is additionally, or alternatively, possible to let the thread bottoms form said angular relationship.

In the illustrated example, the leading portion 12a of the first fixture 10a is substantially cylindrical. In the leading portion 12a, the radial distance from the fixture axis C to a thread top is $r_{t1}$ and the radial distance from the fixture axis C to a thread bottom is $r_{b1}$.

Furthermore, in the illustrated example, the trailing portion 16a is also substantially cylindrical. In the trailing portion the radial distance from the fixture axis C to a thread top is $R_{t1}$ and the radial distance from the fixture axis C to a thread bottom is $R_{b1}$. At least one of the ratios $$\frac{R_{t1} - r_{t1}}{r_{t1}} \text{ and/or } \frac{R_{b1} - r_{b1}}{r_{b1}}$$

is in the range of 0.01-0.3.

For instance, $r_{t1}$ may be 2 mm and $R_{t1}$ may be 2.1 mm, which would result in a ratio of 0.05.

Although, FIG. 3a illustrates that an apical portion 22a of the leading portion 12a is slightly tapering in the apical direction and is provided with one or more cutting edges 24a, other alternatives are also conceivable, e.g. a tapering or non-tapering apical portion without cutting edges.

Furthermore, one or more cutting edges 26a are provided at the border zone of the macrothreads 18a and microthreads 20a, in order to allow the multi-start microthreads 20a to cut female threads into the bone tissue. In the female microthreads created in the bone, the microthreads of the transition portion 14a and trailing portion 16a will pass and will apply a pressure to the bone tissue, resulting in a static tensile strain.

As may be seen in the enlarged view of FIG. 1a, the transition portion has an axial length L, and widens the fixture by $2 \cdot (R_{t1} - r_{t1})$.

FIG. 3b illustrates the second fixture 10b having substantially the same features as the first fixture 10a. For instance, the axial length of the transition portion 14b is L also for the second fixture 10b. However, the widening $2\cdot(R_{t2}-r_{t2})$ of the second fixture 10b is larger than the widening $2\cdot(R_{t1}-r_{t1})$ of the first fixture 10a. In other words, although the radial distance $r_{t2}$ from the centre axis to the thread tops in the leading portion 12b of the second fixture 10b may be equal to said radial distance $r_{t1}$ in the first fixture 10a, the radial distance $R_{t2}$ from the centre axis to a thread top in the trailing portion 16b in the second fixture 10b is larger than corresponding radial distance $R_{t1}$ in the first fixture 10a. Thus, all other factors and parameters being equal, the second fixture 10b would provide a larger tensile strain to the bone tissue than the first fixture 10a. Thus, the first fixture 10a may be used for patients having lower bone quality while the second fixture 10b may be used for patients having higher bone quality.

In both fixtures 10a, 10b, the microthreads 20a, 20b extend uninterrupted along the transition portion 14a, 14b, i.e. the microthreads 20a, 20b extend uninterrupted from the leading portion 12a, 12b to the trailing portion 16a, 16b.

Although only two fixtures 10a, 10b have been illustrated in the set of fixtures in FIGS. 3a-3b, it should be understood that the set could have three, four, five, six or even more fixtures each dimensioned to provide different tensile strain to the bone tissue. The fixtures in FIGS. 3a-3b may suitably have the thread profile illustrated in FIGS. 4a-4b.

FIGS. 4a-4b illustrate a detail of a fixture from a set of fixtures according to at least one example embodiment of the invention. In particular a part of the fixture is shown in cross-section, wherein the fixture has a leading portion 232, a coronally widening transition portion 234 and a substantially straight trailing portion 236. The leading portion 232 is provided with macrothreads 238 having thread tops 240 with a certain radius of curvature a. The thread tops 240 are flanked by apical and coronal flank portions 242a, 242b at a certain acute angle γ relative to a plane perpendicular to the central fixture axis. The angle γ lies in the plane containing the fixture axis. In this case the apical and coronal flanks 242a, 242b are illustrated as having the same angle γ. However, in alternative embodiments the coronal and apical flank angles may differ from each other. The macrothread 238 is provided with a cutting feature, such as a cutting edge 244, to make a corresponding female macrothread in the bone tissue.

Coronally of the macrothreads 238, the leading portion 232 is also provided with double-spiraled microthreads 246 which continue into the transition portion 234 and the trailing portion 236. The microthreads 246 have the same lead as the macrothread 238, the pitch being half the pitch of the macrothread 238. A cutting feature 248 is present at the microthreads in the leading portion 232 to make corresponding female microthreads in the bone tissue. In the illustrated embodiment, throughout the leading portion 232, transition portion 234 and trailing portion 236, the tops 250 of the microthreads 246 have the same radius of curvature as the radius of curvature a of the macrothreads 238. Also, the flank angles of the microthreads 246 correspond to those of the macrothreads 238. The effect of this conformation to the macrothreads 238 will now be explained.

The microthreads 246 are provided as two thread spirals, herein referred to as a first thread spiral 246a and a second thread spiral 246b. The first thread spiral 246a will follow the path of the macrothreads 238. The second thread spiral 246b will make its own path. The cutting feature 244 at the macrothread 238 creates a female thread profile in the bone having the same radius of curvature a and the flank angles γ as the macrothread 238. Thus, when the first thread spiral 246a of the microthreads 246 enters the female bone thread it can theoretically be in full contact with the bone, since the thread tops have the same radius of curvature a and the flanks have the same angles γ as the female bone thread. This means that the initial stability of the fixture can be higher than if the first thread spiral of the microthreads would not fill out the space of the female bone thread. It should be noted that while the cutting features 248 at the microthreads 246 will make a new path for the second thread spiral 246b, it will just adapt the inner areas of the already made female bone thread to conform with the inner areas of the first thread spiral 246a.

It should be understood that the thread profiles shown in FIGS. 4a and 4b, having the same radius of curvature a and the same flank angles for the microthread tops and the macrothread tops, may also be applied to the subsequently illustrated embodiments in the following figures. Thus, the various embodiments illustrated herein may be modified so that the tops of the microthreads and macrothreads have the same radius of curvature and the same flank angles.

Figure 5A:
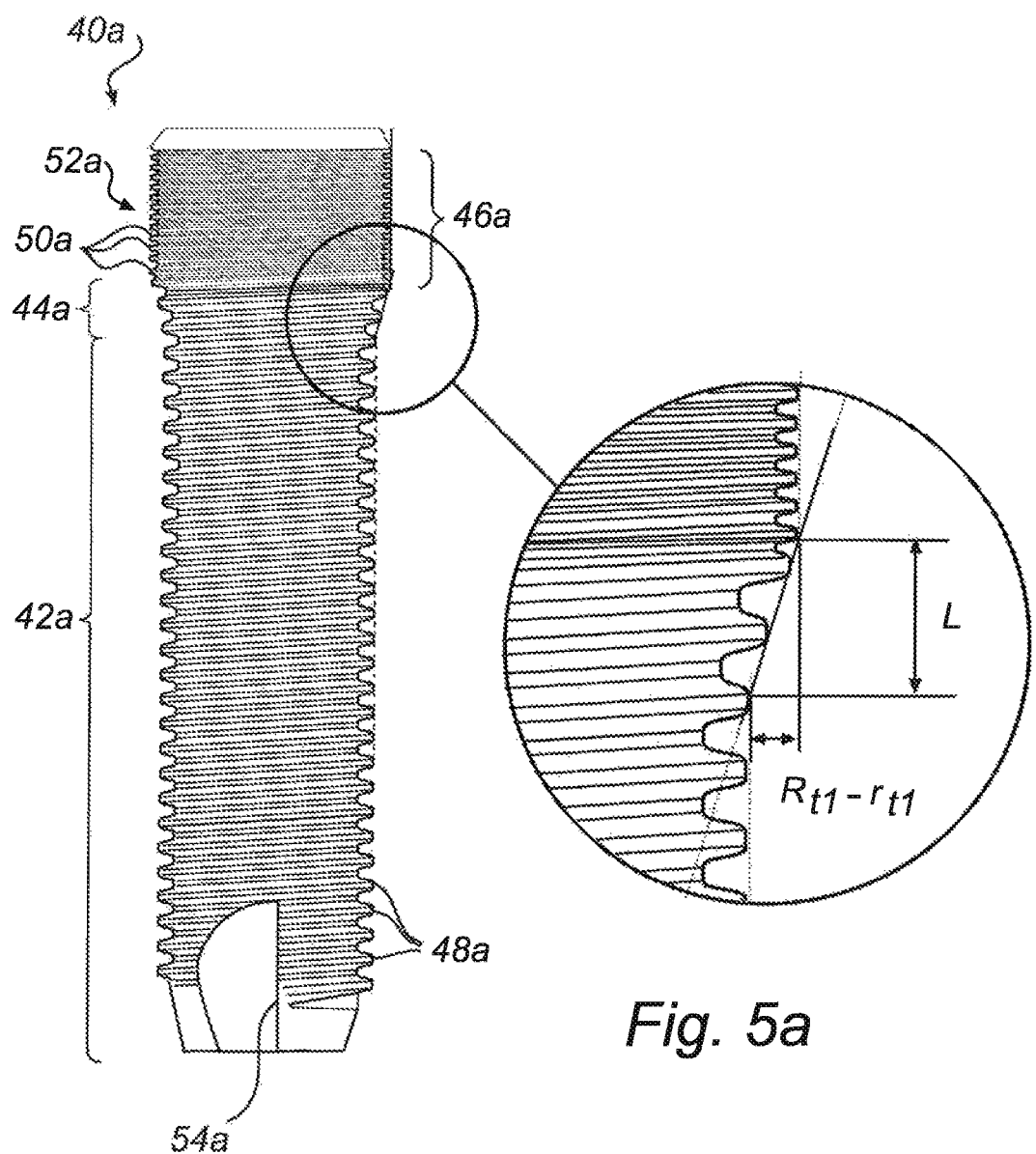
FIG. 5a illustrates a set of fixtures according to at least another example embodiment of the invention.
Figure 5B:
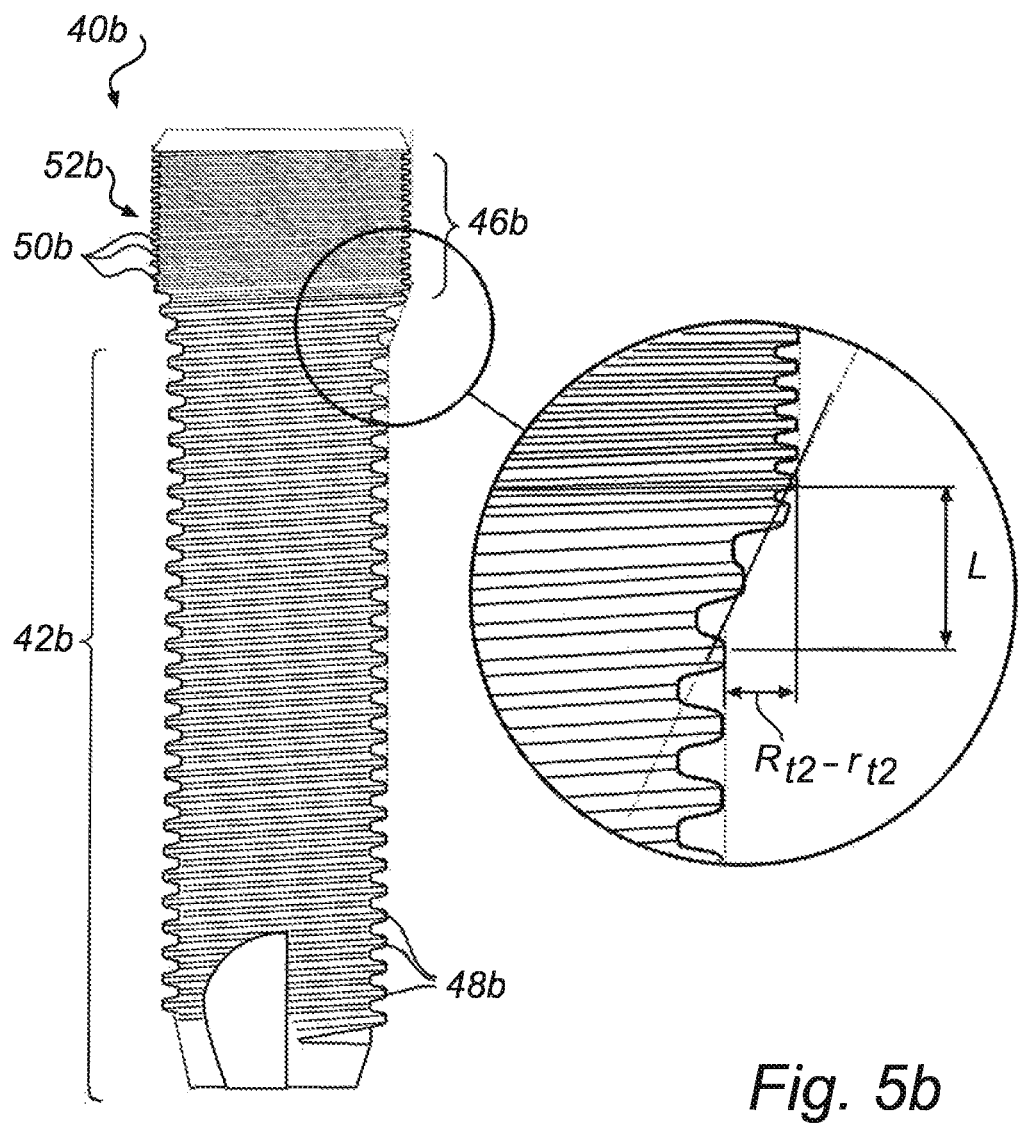
FIG. 5b illustrates a set of fixtures according to at least another example embodiment of the invention.

FIGS. 5a-5b illustrate a set of fixtures 40a, 40b according to at least another example embodiment of the invention. Similarly to the set of fixtures 10a, 10b in FIGS. 3a-3b, the fixtures 40a, 40b in FIGS. 5a-5b are provided with comparatively large macrothreads 48a, 48b along the major part of the axial extension of the fixture threading, and coronally of the macrothreads 48a, 48b are comparatively smaller microthreads 50a, 50b. The microthreads 50a, 50b are located at what may be regarded as a collar portion 52a, 52b. While in the fixtures 10a, 10b of FIGS. 3a-3b the widening of the fixtures started at the microthreads 20a 20b, in FIGS. 5a-5b the widening of the fixtures starts at the macrothreads 48a, 48b.

Thus, with reference to FIG. 5a, the fixtures 40a has a leading portion 42a provided with at least one cutting edge 54a or cutting recess for cutting a female thread into the bone tissue. As the fixture 40a is advanced into the bone tissue and the widening transition portion 44a enters the path created by the cutting edge 54a and the macrothreads 48a in the leading portion, the transition portion 44a will start to press the bone tissue radially. Finally, the trailing portion 46a enters the bone tissue, the trailing portion 46a being substantially cylindrical and will therefore provide a substantially static tensile strain to the bone tissue.

The fixture 40b in FIG. 5b is similar to the fixture 40a in FIG. 5a, however, the widening of the fixture 40b is greater in FIG. 5b. Thus, the difference in diameter, i.e. $2\cdot(R_{t2}-r_{t2})$, between the trailing portion 46b and the leading portion 42b is higher in the fixture 40b in FIG. 5b compared to the corresponding difference in diameter, i.e. $2\cdot(R_{t1}-r_{t1})$, in the fixture 40a of FIG. 5a. Thus, in practice, if $$\frac{R_{t2}-r_{t2}}{r_{t2}} > \frac{R_{t1}-r_{t1}}{r_{t1}},$$

then the fixture 40a of FIG. 5a is used for bone of comparatively lower quality (because it provides lower tensile strain to the bone), while the fixture 40b of FIG. 5b is used for bone of comparatively higher quality (because it provides higher tensile strain to the bone).

Figure 6A:
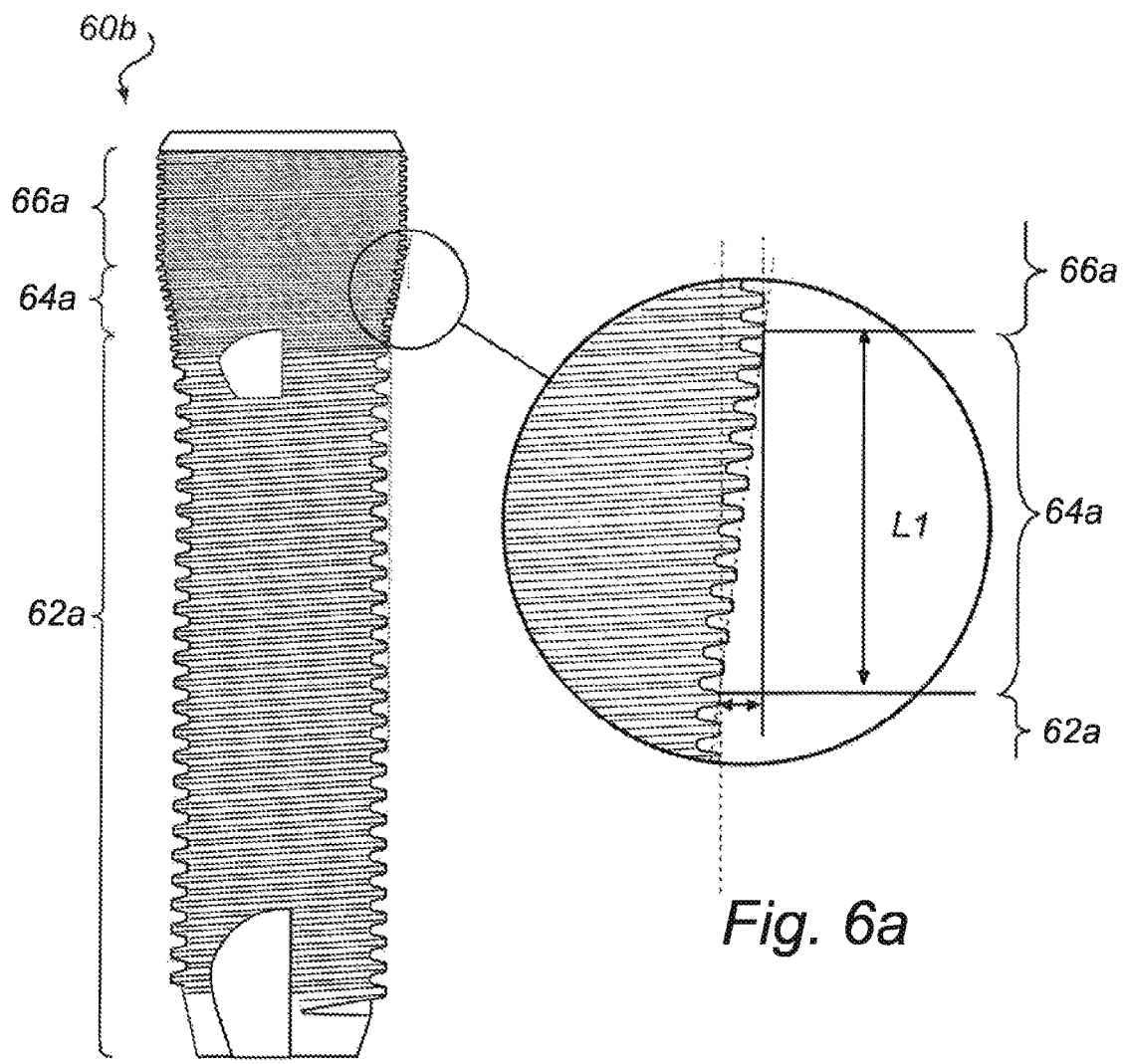
FIG. 6a illustrates a set of fixtures according to at least a further example embodiment of the invention.
Figure 6B:
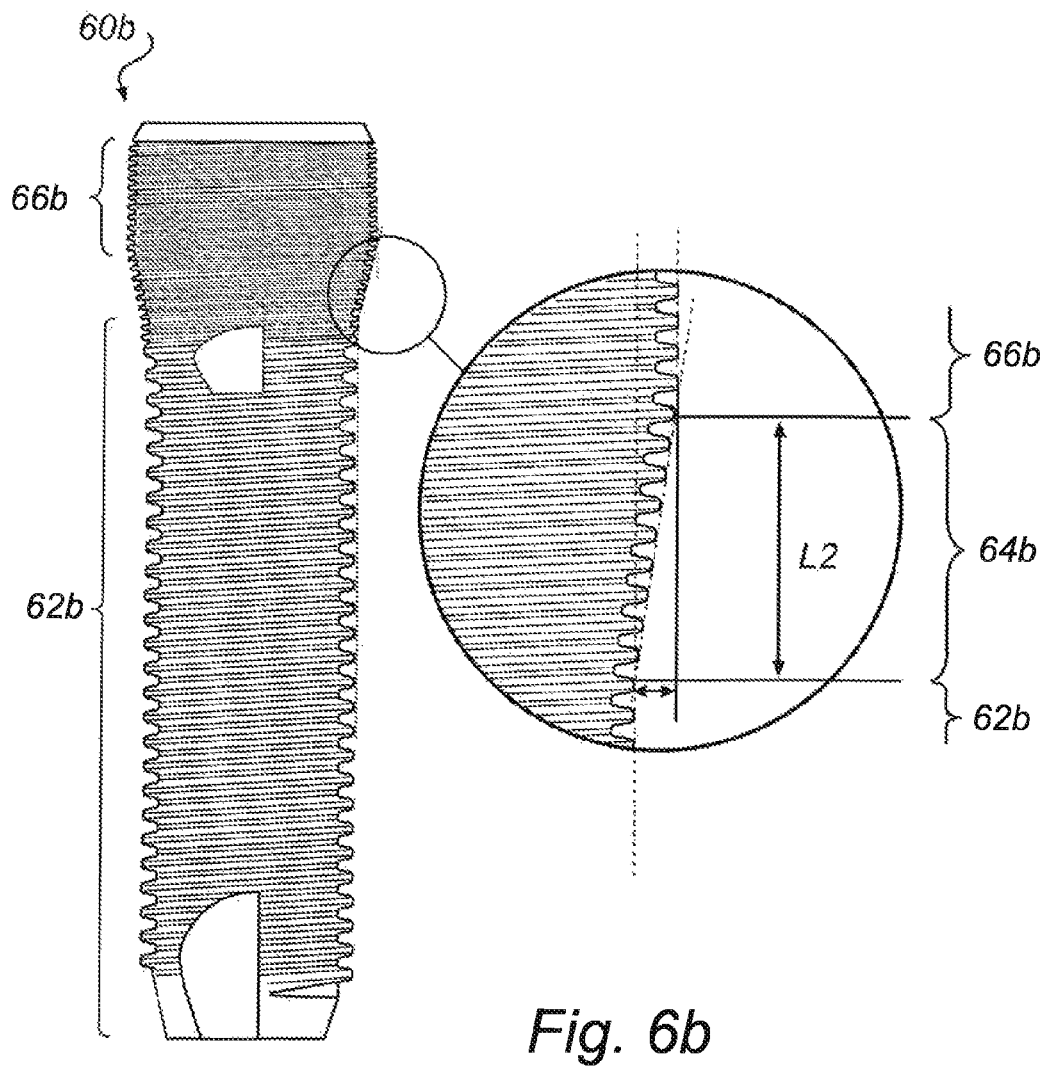
FIG. 6b illustrates a set of fixtures according to at least a further example embodiment of the invention.

FIGS. 6a-6b illustrate a set of fixtures 60a, 60b according to at least a further example embodiment of the invention. While the previous illustrations have shown that the diameter difference between the trailing portion and the leading portion may be varied among the fixtures in a set, FIGS. 6a-6b illustrate two fixtures 60a, 60b in which the difference in width between the trailing portion 66a, 66b and leading portion 62a, 62b is same for both fixtures 60a, 60b. Instead the length of the transition portion 64a, 64b differs between the fixtures 60a, 60b.

Starting with FIG. 6a, as can be seen in the enlarged detailed view, the transition portion 64a widens the fixture 60a at a relatively small angle, thus extending a relatively long distance L1 before reaching the width of the trailing portion 66a. Therefore, in this set of fixtures, the trailing portion 66a in FIG. 6a will have a relatively short axial extension, and accordingly the static strain provided by the trailing portion 66a will be confined to a relative small area of the bone.

Turning now to FIG. 6b, as can be seen in the enlarged detailed view, the transition portion 64b widens the fixture at a relatively large angle, thus extending a relatively short distance L2 before reaching the width of the trailing portion 66b. Therefore, in this set of fixtures, the trailing portion 66b in FIG. 6b will have a relatively long axial extension, and accordingly the static strain provided by the trailing portion will be confined to a relatively large area of the bone.

It should be understood that the difference in width of the trailing portions of the fixtures in a set (shown in e.g. FIGS. 3a-3b) and FIGS. 5a-5b) and the difference in length (shown in e.g. FIGS. 6a-6b) may be combined in a set of fixtures according to at least one example embodiment. Furthermore, not only the transition portions may have different lengths, but additionally (or alternatively) the lengths of the trailing portions may differ between the fixtures.

FIGS. 7a-7d illustrate a set of fixtures 70a-70d according to at least another example embodiment of the invention. In the illustrated set, four fixtures 70a-70d are presented. However, it should be understood that a set could, alternatively, include fewer or more fixtures.

Each one of the four fixtures 70a-70d have different properties with regard to their function of providing static strain to the bone. However, they all have in common that they have double strain-creating zones, which are axially separated from one another.

For purely illustrative purposes the fixtures 70a-70d in the drawings are shown in a partial split view with a an apical section and a coronal section. In between these two sections there is an intermediate section which is not illustrated in the figures.

Figures 7A, 7B:
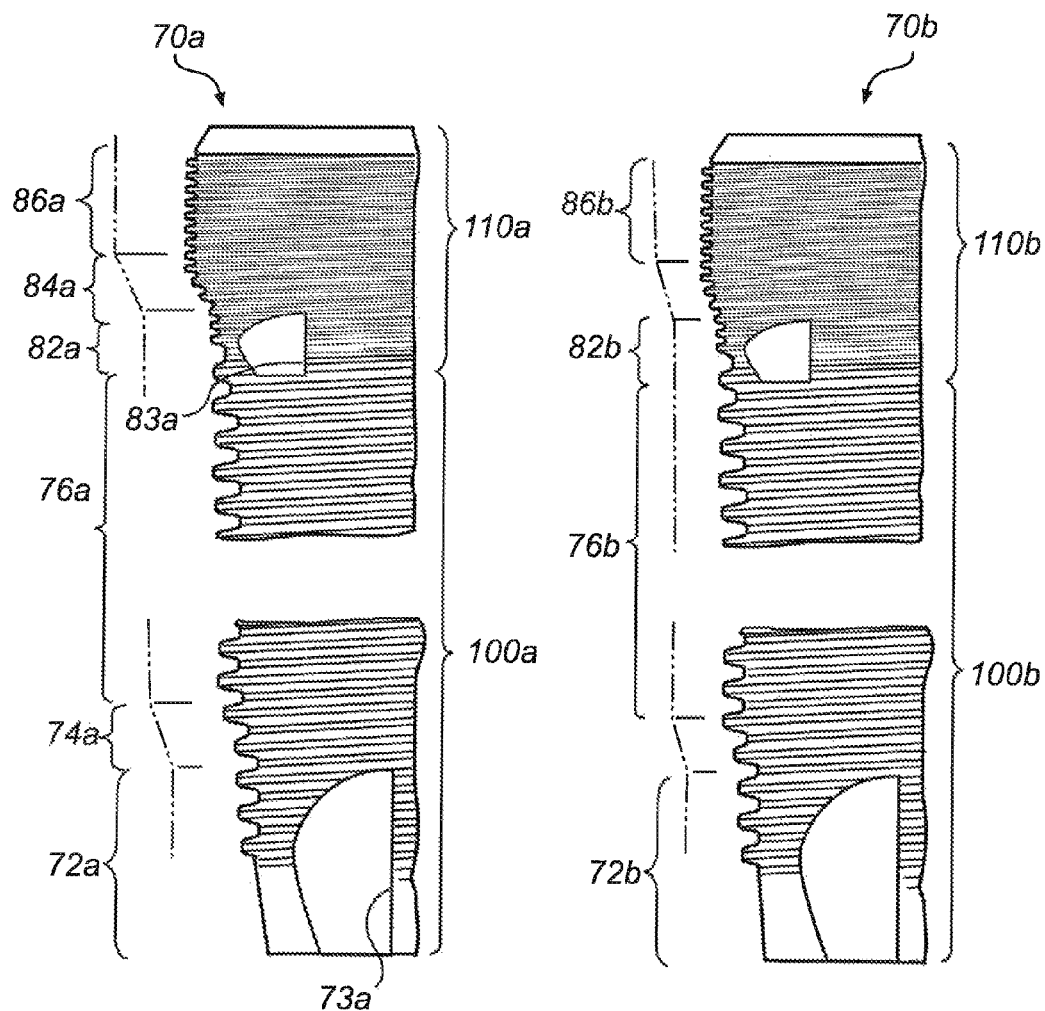
FIG. 7a illustrates a set of fixtures according to at least another example embodiment of the invention.
FIG. 7b illustrates a set of fixtures according to at least another example embodiment of the invention.

Starting with FIG. 7a, the fixture 70a comprises an apical cutting portion 72a having at least one cutting edge 73a for cutting a female thread into the bone tissue. The apical cutting portion 72a thus has the function of the previously discussed leading portions. Thus, the apical cutting portion 72a can be regarded as a first leading portion. The fixture 70a also comprises an apical condensation portion 76a for providing a static strain to the bone tissue and being located coronally of the apical cutting portion 70a. The apical condensation portion 76a thus has the function of the previously discussed trailing portions. Accordingly, the apical condensation portion 76a can be regarded as a first trailing portion. In between the apical cutting portion 72a and the apical condensation portion 76a there is located an apical transition portion 74a which widens the fixture 70a in the coronal direction.

Continuing still with FIG. 7a, the fixture 70a further comprises a coronal cutting portion 82a, having at least one cutting edge 83a, for cutting a female thread into the bone tissue and being located coronally of the apical condensation portion 76a. Thus, the condensation of the bone and the strain provided to the bone by the apical condensation portion 76a will extend substantially from the coronal end of the cutting edge 73a in the apical cutting portion 72a to the apical end of the cutting edge 83a in the coronal cutting portion 82a. The coronal cutting portion 82a may be regarded as a second leading portion. The fixture also comprises a coronal condensation portion 86a for providing a static strain to the bone tissue and being located coronally of the coronal cutting portion 82a. The coronal condensation portion 86a can thus be regarded as a second trailing portion. In between the coronal cutting portion 82a and the coronal condensation portion 86a there is located a coronal transition portion 84a which widens the fixture 70a in the coronal direction.

For facilitating the following discussion, the apical cutting, transition and condensation portions 72a, 74a and 76a, respectively, will commonly be referred to as an apical strain-creating zone 100a. The coronal cutting, transition and condensation portions 82a, 84a, and 86a, respectively, will commonly be referred to as a coronal strain-creating zone 110a. Thus, the fixture 70a in FIG. 7a has double strain-creating zones 100a and 110a, which are located at different axial locations along the fixture 70a.

The fixtures 70b-70d of FIGS. 7b-7d also have these double strain-creating zones. In other words, each of the fixtures 70b-70d in FIGS. 7b-7d, have corresponding apical cutting, transition and condensation portions (present in an apical strain-creating zone), and coronal cutting, transition and condensation portions (present in the coronal strain-creating zone). It should be understood that the drawings are schematic and not necessarily true to scale. For instance, since the cancellous bone tissue is less brittle compared to cortical bone, the apical strain-creating zones may suitably be dimensioned to provide a higher strain than the coronal strain-creating zones.

In the fixture 70b in FIG. 7b both the coronal and the apical strain-creating zones 100b and 110b are different compared to the corresponding zones 100a and 100b in the fixture 70a in FIG. 7a. More specifically, the fixture 70b in FIG. 7b is not widened as much as the fixture 70a in FIG. 7a. Thus, in the fixture 70b of FIG. 7b the diameter difference between the apical condensation portion 76b and the apical cutting portion 72b in FIG. 7b is smaller than the corresponding diameter difference for the fixture 70a in FIG. 7a. Likewise, the diameter difference between the coronal condensation portion 86b and the coronal cutting portion 82b in FIG. 7b is smaller than the corresponding diameter difference for the fixture 70a in FIG. 7a. Thus, both strain-creating zones 100a, 110a in FIG. 7a provide a larger strain to the bone tissue compared to the strain-creating zones 100b, 110b of the fixture 70b in FIG. 7b.

Although, FIG. 7b illustrates that the fixture 70b is arranged to provide lower strain from both strain-creating zones 100b, 110b compared to the corresponding zones 100a, 110a of the fixture 70a in FIG. 7a, it should be understood that among a set of fixtures numerous variations are conceivable, some of which are illustrated in FIGS. 7c-7d.

FIG. 7c illustrates a fixture 70c having an apical strain-creating zone 100c corresponding to that (100b) of the fixture 70b in FIG. 7b and a coronal strain-creating zone 110c corresponding to that (110a) of the fixture 70a in FIG. 7a.

FIG. 7d illustrates a fixture 70d having an apical strain-creating zone 100d corresponding to that (100a) of the fixture 70a in FIG. 7a and a coronal strain-creating zone 110d corresponding to that (110b) of the fixture 70b in FIG. 7b.

It should be understood that although FIGS. 7a-7d have illustrated only two alternative widths for both the coronal and the apical condensation portions, it should be understood that other alternatives are also conceivable. For instance, a fixture in the set could, in at least one of the coronal and apical strain-creating zones, have an even smaller widening than the fixture 70b in FIG. 7b or a larger widening than the fixture 70a in FIG. 7a.

Figure 8A:
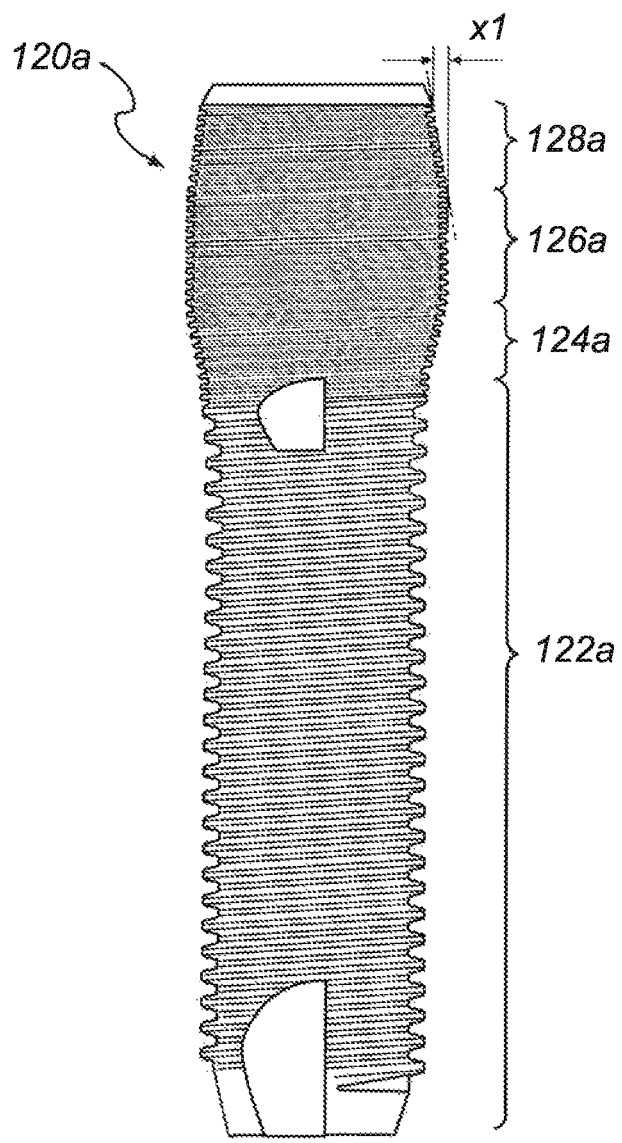
FIG. 8a illustrates a set of fixtures according to at least yet another example embodiment of the invention.
Figure 8B:
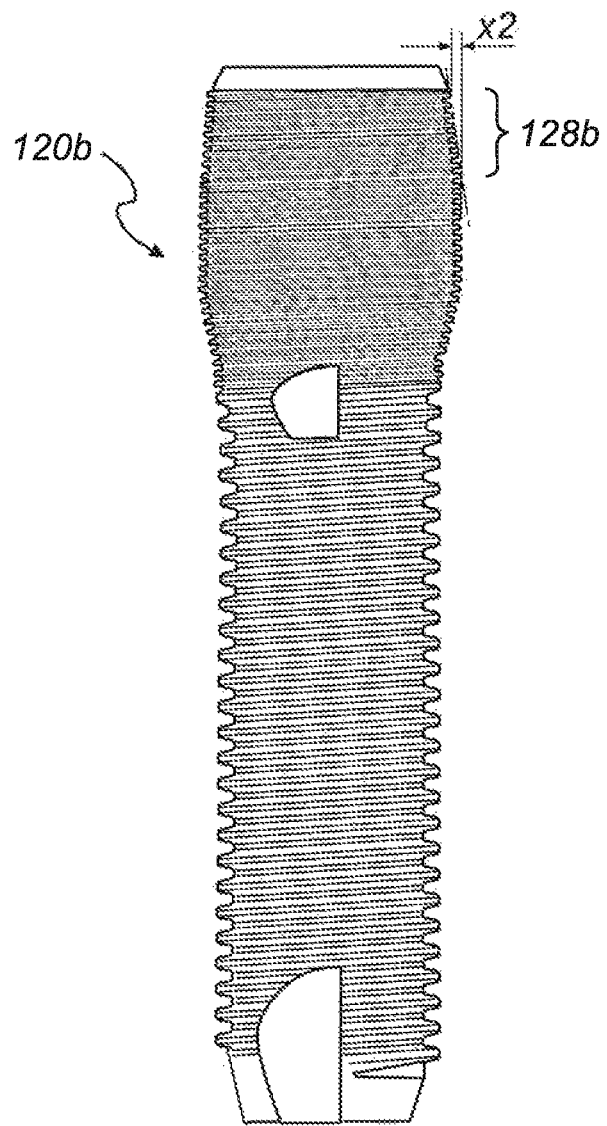
FIG. 8b illustrates a set of fixtures according to at least yet another example embodiment of the invention.

FIGS. 8a-8b illustrate a set of fixtures 120a, 120b according to at least yet another example embodiment of the invention.

Similarly to the previously discussed fixtures, the fixture 120a in FIG. 8a comprises a leading portion 122a, a transition portion 124a and a trailing portion 126a. The trailing portion 126a is adapted to provide a tensile strain to the bone. Coronally adjacent to the trailing portion 126a the fixture 120a has a threaded coronally tapering portion 128a, which will provide relief (denoted as a distance x1 in FIG. 8a) for the coronal-most bone and allow it to flex back towards the fixture 120a. Thus, this allows the tensile strain to be varied along the axial direction of the fixture 120a. In FIG. 8b the angle of tapering is smaller than in FIG. 8a. Consequently, the coronally tapering portion 128b in FIG. 8b will provide less relief (denoted as a smaller distance x2 in FIG. 8b) to the coronal-most bone. Thus, the FIG. 8a fixture 120a may suitably be selected for use in relatively brittle marginal bone while the FIG. 8b fixture 120b may suitably be selected for use in relatively less brittle marginal bone.

An alternative to a coronally tapering portion, would be to have some other shape, e.g. cylindrical, the width of which is smaller than the width of the trailing portion.

In at least another embodiment, the fixture could be designed so that the trailing portion is adapted to provide a certain tensile strain to the cancellous bone, and then a narrower coronally following portion is present to provide a lower tensile strain to the cortical bone. It should be understood that anyone of the previously discussed and illustrated embodiments could be modified to present a narrower portion coronally of a trailing portion in order to provide a variation of strain in the axial extension of the fixture.

FIGS. 9a-9d illustrate an implantation system according to at least one example embodiment of the invention. The implantation system comprises a fixture 200 (FIGS. 9c-9d) and two separate thread makers 240a, 240b (FIGS. 9a-9b). FIGS. 9c-9d illustrate that the externally threaded fixture 200 has a leading portion 212 and a wider trailing portion 216 (see FIG. 9d). A transition portion 214 interconnects the leading portion 212 with the trailing portion 216. FIG. 9a illustrates the first separate externally threaded thread maker 240a having at least one cutting edge 244a for making a female thread in the bone tissue, which female thread is adapted to mate with the thread of the fixture 200. FIG. 9b illustrate a second separate externally threaded thread maker 240b having at least one cutting edge 244b for making a female thread in the bone tissue, which female thread is adapted to mate with the thread of the fixture 200. In the first thread maker 240a, the largest radial distance from the centre axis to a thread top and/or thread bottom of said cutting edge 244a is different from the largest radial distance from the centre axis to a thread top and/or thread bottom, respectively, of the cutting edge 244b of the second thread maker 240b. For instance, the first thread maker 240a has a major diameter d1 which is different from a major diameter d2 of the second thread maker 240b.

The female thread in the bone tissue made by either one of the first or second thread makers 240a, 240b has a first portion for receiving the leading portion 212 of the fixture 200 and a second portion for receiving the trailing portion 216 of the fixture 200. The diametrical difference between the leading portion 212 and said first portion is smaller than the diametrical difference between the trailing portion 216 and said second portion (the comparison being made with respect to major and/or minor fixture diameter and corresponding major and/or minor bore hole diameter). Thereby, the trailing portion 216 will provide a static strain to the bone tissue.

With respect to the above, it would for instance be conceivable to make a cylindrical bore hole and then select one two thread makers 240a, 240b. As an example the first thread maker 240a may provide a female thread having substantially the same major diameter d1 as that of the leading portion 212 of the fixture 200, wherein only the wider trailing portion 216 will act to condense the bone tissue. The second thread maker 240b may provide a female thread having slightly smaller major diameter d2 compared to the leading portion 212 of the fixture 200, wherein the leading portion 212 will cause a slight condensation of the bone and the wider trailing portion 216 will cause a larger condensation of the bone. Alternatively, the second thread maker 240b may be designed such that it provides a female thread having slightly larger major diameter compared to the leading portion 212 of the fixture 200, in case of which only the trailing portion 216 will condense the bone.

Although the present disclosure has mainly focused on dental fixtures, it should be understood that the invention is not so limited, but may also be used for providing strain to other bone tissue than in the jawbone. For instance, the invention also encompasses orthopedic applications.

The invention claimed is:

1. A set of fixtures for installation in bone tissue, comprising
 a first fixture for insertion into a bore hole arranged in bone tissue for providing static strain to the bone tissue, and
 a second fixture for insertion into a bore hole arranged in bone tissue for providing static strain to the bone tissue, wherein the static strain provided by the first fixture if installed into a bore hole is, at least with respect to magnitude and/or axial extension, different from the static strain provided by the second fixture if the second fixture would be installed into said bore hole instead of the first fixture,
 wherein each one of said fixtures comprises a leading portion and a wider trailing portion for providing the static strain to the bone tissue, wherein the axial length of the trailing portion of the first fixture is longer than the axial length of the trailing portion of the second fixture, whereby the static strain in the bone is applied over a longer axial distance if the first fixture is installed compared to if the second fixture is installed.

2. The set as in claim 1, wherein each one of said fixtures comprises
 a leading portion, and
 a trailing portion being wider than the leading portion with respect to major and/or minor fixture diameter for providing the static strain to the bone tissue, wherein at least a subportion of the trailing portion of the first fixture is dimensionally different from a corresponding subportion of the trailing portion of the second fixture.

3. The set as in claim 2, wherein each one of said fixtures comprises an external thread which extends uninterrupted from the leading portion to the trailing portion.

4. The set as in claim 2, wherein said leading and trailing portions of said fixtures comprise a respective outer surface being threaded for engagement with the bone tissue, wherein thread tops and thread bottoms are provided alternatingly along the axial direction of the fixture, wherein
 in said subportion of the trailing portion of the first fixture, the radial distance from the fixture axis to a thread top is $R_{t1}$ and the radial distance from the fixture axis to a thread bottom is $R_{b1}$, and in said corresponding subportion of the trailing portion of the second fixture, the radial distance from the fixture axis to a thread top is $R_2$ and the radial distance from the fixture axis to a thread bottom is $R_{b2}$, wherein $R_{t1}$ is different from $R_{t2}$, and/or $R_{b1}$ is different from $R_{b2}$.

5. The set as in claim 4, wherein the threading of the leading portion is provided with at least one cutting edge for making a female thread in the bone tissue, wherein, in the leading portion of the first fixture the largest radial distance from the fixture axis to a thread top of said cutting edge is $r_{t1}$ and the largest radial distance from the fixture axis to a thread bottom of said cutting edge is $r_{b1}$, wherein, in the leading portion of the second fixture the largest radial distance from the fixture axis to a thread top of said cutting edge is $r_{t2}$ and the largest radial distance from the fixture axis to a thread bottom of said cutting edge is $r_{b2}$, wherein the relationship $$\frac{R_{t1} - r_{t1}}{r_{t1}}$$

is different from the relationship $$\frac{R_{t2} - r_{t2}}{r_{t2}},$$

and/or the relationship $$\frac{R_{b1} - r_{b1}}{r_{b1}}$$

is different from the relationship $$\frac{R_{b2} - r_{b2}}{r_{b2}}.$$

6. The set as in claim 5, wherein $r_{t1}=r_{t2}$, $r_{b1}=r_{b2}$, or both.

7. The set as in claim 1, wherein each one of said fixtures comprises
a leading portion and a wider trailing portion for providing the static strain to the bone tissue, both the leading portion and the trailing portion comprising a respective outer surface being threaded for engagement with bone tissue, wherein thread tops and thread bottoms are provided alternatingly in the axial direction of the fixtures,
wherein the threading of the leading portion is provided with at least one cutting edge for making a female thread in the bone tissue,
wherein, in the leading portion of the first fixture the largest radial distance from the fixture axis to a thread top of said cutting edge is $r_{t1}$ and the largest radial distance from the fixture axis to a thread bottom of said cutting edge is $r_{b1}$,
wherein, in the leading portion of the second fixture the largest radial distance from the fixture axis to a thread top of said cutting edge is $r_{t2}$ and the largest radial distance from the fixture axis to a thread bottom of said cutting edge is $r_{b2}$, wherein in the trailing portion of the first fixture, the radial distance from the fixture axis to a thread top is $R_{t1}$ and the radial distance from the fixture axis to a thread bottom is $R_{b1}$,
wherein in the trailing portion of the second fixture, the radial distance from the fixture axis to a thread top is $R_{t2}$ and the radial distance from the fixture axis to a thread bottom is $R_{b2}$,
wherein the relationship $$\frac{R_{t1} - r_{t1}}{r_{t1}}$$

is different from the relationship $$\frac{R_{t2} - r_{t2}}{r_{t2}},$$

and/or the relationship $$\frac{R_{b1} - r_{b1}}{r_{b1}}$$

is different from the relationship $$\frac{R_{b2} - r_{b2}}{r_{b2}}.$$

8. The set as in claim 2, wherein each one of said fixtures comprises an intermediate coronally widening transition portion having an apical end which borders to the leading portion and a coronal end which borders to the trailing portion, wherein the transition portion has an axial length L between its apical and coronal ends, wherein any coronal widening of the trailing portions, with respect to the thread tops and/or thread bottoms, is per axial unit length smaller than the coronal widening of the transition portion.

9. The set as in claim 1, wherein both of said fixtures are externally threaded, wherein the axial length of the threading of the first fixture is substantially the same as the axial length of the threading of the second fixture.

10. The set as in claim 1, wherein the static strains provided by said fixtures are in the range of 0.01-0.3.

11. The set as in claim 1, wherein each one of said fixtures comprises
an apical cutting portion for cutting a female thread into the bone tissue,
an apical condensation portion for providing a static strain to the bone tissue and being located coronally of the apical cutting portion,
a coronal cutting portion for cutting a female thread into the bone tissue and being located coronally of the apical condensation portion,
a coronal condensation portion for providing a static strain to the bone tissue and being located coronally of the coronal cutting portion,
wherein at least one of said cutting portions and condensation portions of the first fixture has a different width with respect to major and/or minor fixture diameter compared to the corresponding portion of the second fixture.

12. The set as in claim 1, wherein said fixtures are dental fixtures for arrangement in jawbone.

13. A method of selecting a fixture from a set of at least two fixtures of claim 1, each fixture, compared with the other fixture or fixtures, being adapted to provide a different static strain if inserted into a bore hole in the bone tissue of a person, the method comprising the steps of:
- determining the state or value of a strain-affecting characteristic of a person or a person's bone tissue, and
- selecting a fixture from said set based on the determined state or value.

14. The method as in claim 13, wherein said strain-affecting characteristic is one of: the person's age, bone density, mineral content of the bone tissue, bone tissue disease and bone thickness.

15. A set of fixtures for installation in bone tissue, comprising
- a first fixture for insertion into a bore hole arranged in bone tissue for providing static strain to the bone tissue, and
- a second fixture for insertion into a bore hole arranged in bone tissue for providing static strain to the bone tissue,
- wherein the static strain provided by the first fixture if installed into a bore hole is, at least with respect to magnitude and/or axial extension, different from the static strain provided by the second fixture if it would be installed into said bore hole instead of the first fixture,
- wherein each one of said fixtures comprises a leading portion, and a trailing portion being wider than the leading portion with respect to major and/or minor fixture diameter for providing the static strain to the bone tissue, wherein at least a subportion of the trailing portion of the first fixture is dimensionally different from a corresponding subportion of the trailing portion of the second fixture;
- wherein said leading and trailing portions of said fixtures comprise a respective outer surface being threaded for engagement with the bone tissue, wherein thread tops and thread bottoms are provided alternatingly along the axial direction of the fixture, wherein in said subportion of the trailing portion of the first fixture, the radial distance from the fixture axis to a thread top is $R_{t1}$ and the radial distance from the fixture axis to a thread bottom is $R_{b1}$, and wherein in said corresponding subportion of the trailing portion of the second fixture, the radial distance from the fixture axis to a thread top is $R_{t2}$ and the radial distance from the fixture axis to a thread bottom is $R_{b2}$,
- wherein $R_{t1}$ is different from $R_{t2}$, and/or $R_{b1}$ is different from $R_{b2}$;
- wherein the threading of the leading portion is provided with at least one cutting edge for making a female thread in the bone tissue;
- wherein, in the leading portion of the first fixture the largest radial distance from the fixture axis to a thread top of said cutting edge is $r_{t1}$ and the largest radial distance from the fixture axis to a thread bottom of said cutting edge is $r_{b1}$;
- wherein, in the leading portion of the second fixture the largest radial distance from the fixture axis to a thread top of said cutting edge is $r_{t2}$ and the largest radial distance from the fixture axis to a thread bottom of said cutting edge is $r_{b2}$;
- wherein the relationship $$\frac{R_{t1} - r_{t1}}{r_{t1}}$$

is different from the relationship $$\frac{R_{t2} - r_{t2}}{r_{t2}},$$

and/or the relationship $$\frac{R_{b1} - r_{b1}}{r_{b1}}$$

is different from the relationship $$\frac{R_{b2} - r_{b2}}{r_{b2}};$$

and
- wherein $r_{t1}=r_{t2}$, $r_{b1}=r_{b2}$, or both.

16. A method of selecting a fixture from a set of at least two fixtures 15, each fixture, compared with the other fixture or fixtures, being adapted to provide a different static strain if inserted into a bore hole in the bone tissue of a person, the method comprising the steps of:
- determining the state or value of a strain-affecting characteristic of a person or a person's bone tissue, and
- selecting a fixture from said set based on the determined state or value.

17. The method as in claim 16, wherein said strain-affecting characteristic is one of: the person's age, bone density, mineral content of the bone tissue, bone tissue disease and bone thickness.

* * * * *